(12) United States Patent
Alon

(10) Patent No.: US 11,864,805 B1
(45) Date of Patent: *Jan. 9, 2024

(54) ORTHOPEDIC FASTENER AND ASSOCIATED SYSTEMS AND METHODS

(71) Applicant: Guy Alon, El Paso, TX (US)

(72) Inventor: Guy Alon, El Paso, TX (US)

(*) Notice: Subject to any disclaimer, the term of this patent is extended or adjusted under 35 U.S.C. 154(b) by 307 days.

This patent is subject to a terminal disclaimer.

(21) Appl. No.: 17/227,733

(22) Filed: Apr. 12, 2021

Related U.S. Application Data

(63) Continuation-in-part of application No. 16/434,132, filed on Jun. 6, 2019, now Pat. No. 11,000,326.

(60) Provisional application No. 62/682,430, filed on Jun. 8, 2018.

(51) Int. Cl.
| | |
|---|---|
| A61B 17/86 | (2006.01) |
| A61B 17/70 | (2006.01) |
| A61B 17/56 | (2006.01) |
| A61B 17/68 | (2006.01) |

(52) U.S. Cl.
CPC ........ *A61B 17/863* (2013.01); *A61B 17/7035* (2013.01); *A61B 17/8605* (2013.01); *A61B 2017/564* (2013.01); *A61B 2017/681* (2013.01)

(58) Field of Classification Search
CPC ..... A61B 17/7001; A61B 17/84; A61B 17/86; A61B 17/8625; A61B 17/863; A61B 17/8635; A61B 2017/8655; A61B 17/866; F16B 25/0057; F16B 25/0068; F16B 25/0089

See application file for complete search history.

(56) References Cited

U.S. PATENT DOCUMENTS

| | | | |
|---|---|---|---|
| 7,101,133 B2 * | 9/2006 | Dicke | F16B 25/0057 411/386 |
| 11,000,326 B1 * | 5/2021 | Alon | A61B 17/863 |
| 2015/0044638 A1 * | 2/2015 | Baez | A61C 8/0048 433/174 |

FOREIGN PATENT DOCUMENTS

WO    WO-2016116920 A1 * 7/2016

OTHER PUBLICATIONS

United States Patent and Trademark Office; Notice of Allowance for U.S. Appl. No. 16/434,132; dated Jan. 12, 2021; 9 pages.

* cited by examiner

*Primary Examiner* — Larry E Waggle, Jr.

(74) *Attorney, Agent, or Firm* — Womble Bond Dickinson (US) LLP

(57) ABSTRACT

An orthopedic fastener including a shaft may have a plurality of compound parabolic petals extending helically around the shaft. The petals may be configured for compressing trabecular bone through which the petals are inserted. The shaft may further include one or more force diffusion areas that may more efficiently redirect/distribute radial forces caused by an external force applied to the orthopedic fastener, to keystone portions of trabecular bone compressed respectively against the force diffusion areas.

20 Claims, 14 Drawing Sheets

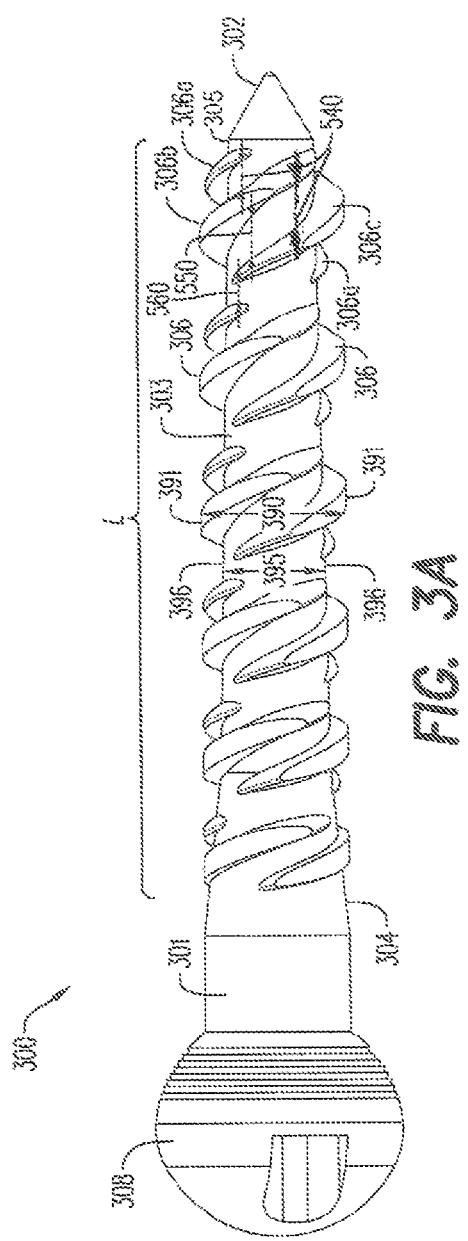
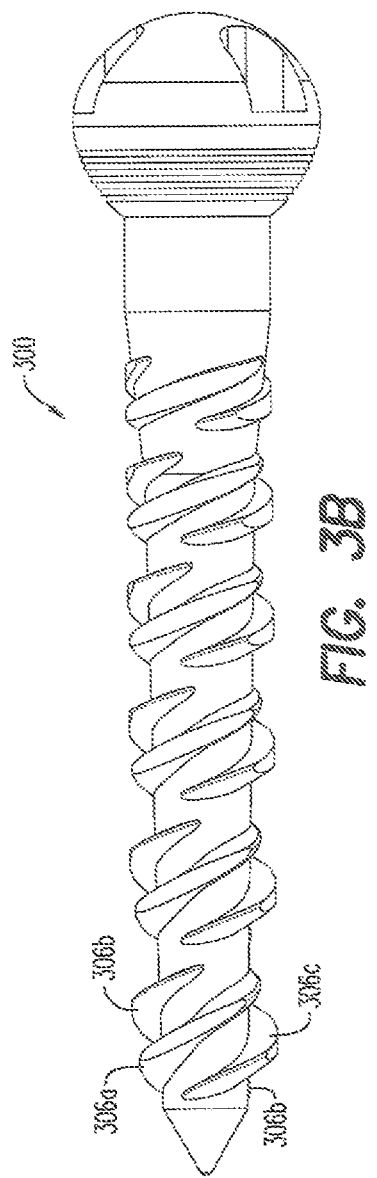
FIG. 3A
FIG. 3B

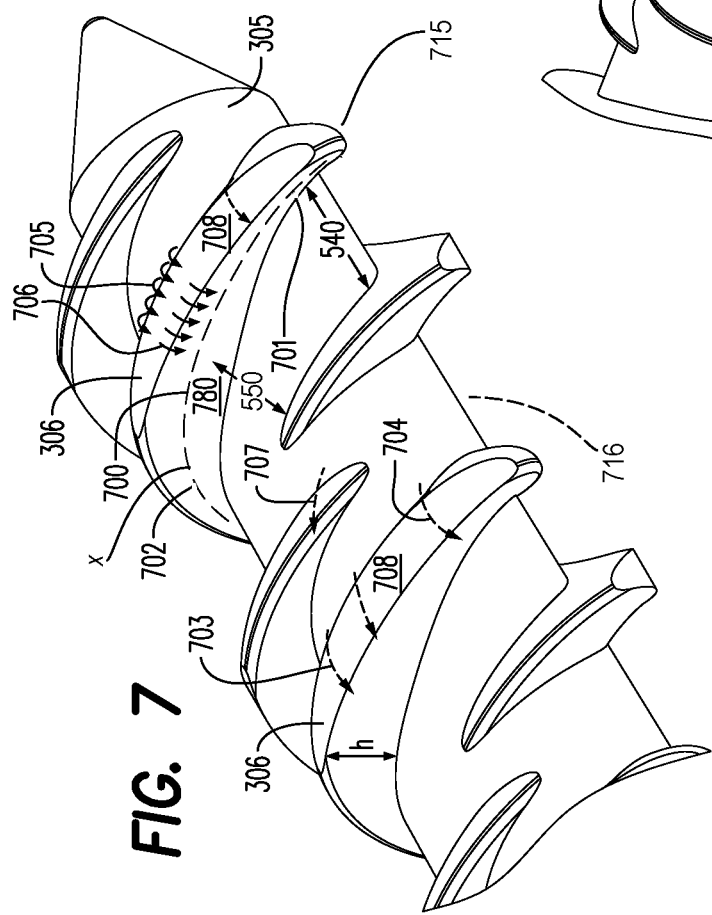

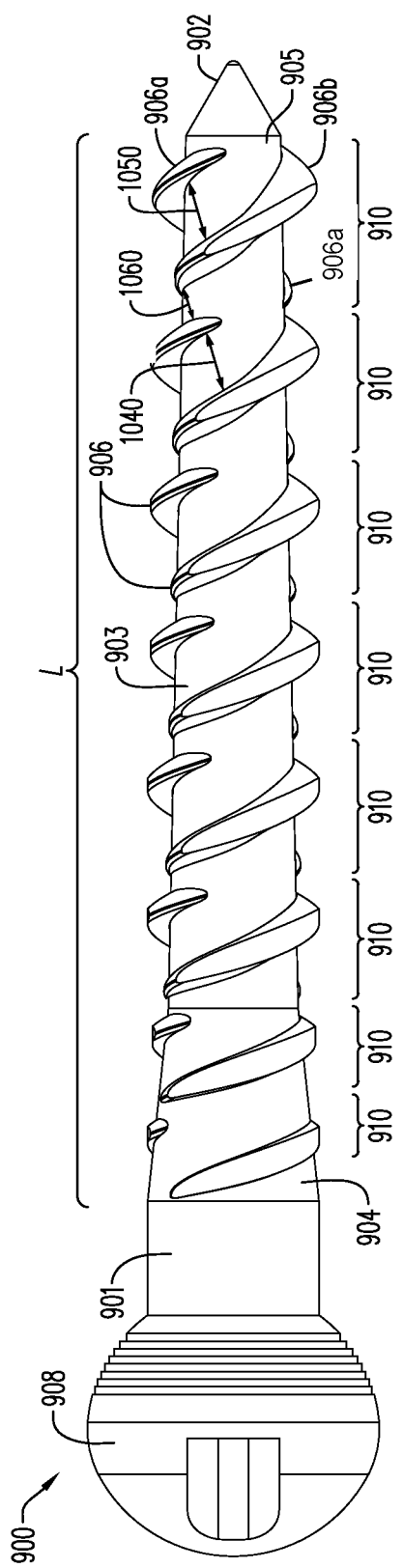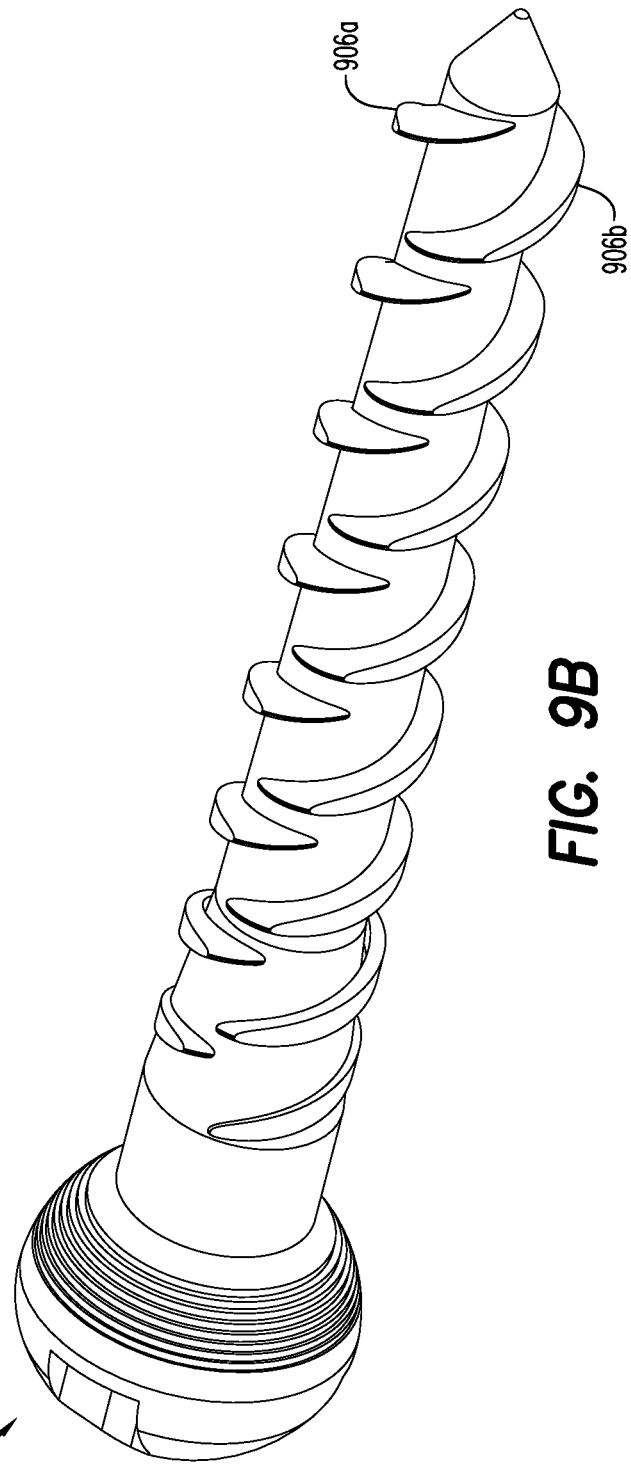

ORTHOPEDIC FASTENER AND ASSOCIATED SYSTEMS AND METHODS

CROSS-REFERENCE TO RELATED APPLICATIONS

This application is a continuation-in-part of and claims priority to U.S. patent application Ser. No. 16/434,132 filed Jun. 6, 2019, which claims the benefit of U.S. Provisional Patent Application No. 62/682,430 filed Jun. 8, 2018. The entire contents of each application listed above are incorporated herein by reference.

BACKGROUND OF THE DISCLOSURE

It is common for trauma, oral and maxillofacial, bone reconstruction, total joint reconstruction, or orthopedic corrective procedures for various deformity (collectively, "orthopedic procedures") to utilize surgical intervention to reconstruct repair injured or failing joints or bones. Often during orthopedic procedures, securing or fastening bones, teeth, tissues, or other devices to bones is necessary. The devices, systems, and methods used to perform these fixations are critical for minimizing patient trauma, disability, and recovery time, and ensuring that the fixation remains secured. In one regard, the devices and methods for these procedures must interact with the specific structure of bone. For example, fasteners must pierce surrounding tissue and the bone and secure therein. Less movement of the fracture ends, fragments, or fixation device typically correlates to shorter healing time, increased stability, and more functional utility of the repair, although complete rigidity is not necessarily desirable.

In one aspect, trabecular bone is a focal point for bone damage during orthopedic procedures. With reference to FIG. 1, trabecular bone 102, also referred to as cancellous bone, is a generally spongy, porous type of bone that is found at the ends of long bones and within flat and irregular bones such as the sternum, pelvis, and spine. Trabecular bone 102 may be contained within denser cortical bone surfaces 101.

FIG. 2 shows finite structures of trabecular bone 102 (with continuing reference to FIG. 1). At the micro-201 and nano-202 structure scales the lattice-type configuration of trabecular bone 102 may be seen. The lattice includes bridges 203 of trabecular bone material (described in further detail, below) with interstices therebetween. Trauma or lacerations to the bone material bridges 203 can weaken entire portions of the lattice. The nano-structure scale 202 shows that successive bridges 203 of bone material may be supported by and/or connected to other discrete formations within the trabecular bone 102. Thus, damage to one portion of the lattice may affect the integrity of other portions.

Each trabecular bone cell also includes nucleotides which provide a communication channel between trabecular bone cells within a larger bone structure. Accordingly, minimizing the scar tissue in the insertion area and leveraging the nucleotide connections between all bone cells in a given bone structure is important since it allows for the bone to leverage the natural characteristics of bone and encourage adjacent cells to come to the aid of any impacted cells and provide additional anchoring stability in the overall bone structure. This is especially important when surgical fasteners and other orthopedic fixation devices are used on the bone to correct deformity and require maximum stability for thorough healing.

All of the above aspects of trabecular bone are susceptible to damage during orthopedic procedures of all kinds. For example, to fix an orthopedic device to a bone a surgeon may drill an insertion point through one of the cortical bone surfaces, advance a fastener through the insertion point and trabecular bone to secure the orthopedic device, and anchor the fastener in the cortical wall distal to the insertion point. A fastener that must pierce and secure itself within the trabecular bone can potentially traumatize or lacerate the trabecular bone and/or damage the nucleotide connections between trabecular bone cells.

Damage to the trabecular bone can increase healing time and scar tissue. This, in turn, reduces the effectiveness of the repair as the bone attempts to adjust to any fasteners, fixtures, or manipulations from the orthopedic procedure. Further, trabecular bone injury weakens the entire bone and hinders the natural biological bone remodeling whereby the trabecular bone structure naturally changes over the course of the bone's life and adjusts to or prevents further damage from repeated forces. Damage to the trabecular bone stimulates a rigid bone remodeling to compensate for the damage. The damaged portions of trabecular bone become incapable of natural bone remodeling. Thus, more damage to the natural structure of the trabecular bone leads to more bone with diminished ability to adjust to repeated forces and/or prevent further damage or injury.

Current screws, fasteners, and other devices used in orthopedic procedures can damage the trabecular bone. For example, the devices may manipulate and artificially fixate bone fragments including trabecular bone to fix the device(s) in place. The manipulation and fixation may traumatize the trabecular bone by, e.g., indiscriminately stressing, fracturing, and shifting portions of the bone. In addition, some screws and fasteners employ sharp threading that can lacerate the trabecular bone and surrounding tissues.

In addition, the devices and systems used in the subject procedures often fracture, loosen, or even disengage from fixations. Any of these can cause further damage to the bone and may require additional orthopedic procedures to remedy.

The current devices, systems, and associated methods also have some difficulty interfacing with many patient co-morbidities: osteopenia and osteoporosis, Parkinson's Disease, diabetes mellitus, among others.

Further, as mentioned above, preserving "healthy" bone, i.e., bone retaining its natural structure, is an important factor in the healing and future function of the bone. In addition to inserting an implant, many forces (generally, and without limitation, "external forces") may act on the implant after insertion and cause damage to the bone. Implants that may be especially subject to external forces after insertion include, without limitation, shoulder anchors, dental implants, spinal implants, and knee implants. The external forces may be, e.g., vectored (i.e., acting in a specific direction), bidirectional, omnidirectional, and/or circular (or otherwise shaped) relative to an axis of the implant. The external forces may be from innumerable physiological or non-physiological events or conditions. For example, an external force may be caused by physiological conditions like body weight (i.e., body mass under the force of gravity), events like movements through joints, and/or use like chewing. An external force may also be caused by a non-physiological event, like falls and acute injuries, and/or combined events, like walking/running, which incorporates physiological movement and also cause impact forces from the ground.

Forces from particular movements and functions may also be harmonic—i.e., they may have a direction and/or shape, and intensity, and a frequency at which the forces repeat. For example, walking, sitting, chewing, and the like generate harmonic forces that may act on an implant.

Whether harmonic or discrete, external forces on an implant may damage bone structure that supports or surrounds the implant. For example, an external force acting on a portion of the implant may diffuse through the implant as radial forces. "Radial forces" refers generally to forces that have a direction including, at least in part, a divergence from, e.g., a center axis of the implant. Radial forces that diffuse through the implant may ultimately encounter a counterforce point of the implant. A counterforce point may exert or experience a counterforce against the radial force. Accordingly, bone structure supporting the implant at or near the counterforce point may be subject to stress or damage from, e.g., absorbing, deflecting, or dissipating the radial force, and/or a crushing force of the implant, at the counterforce point.

In some conventional implants, i.e., screws, the external force may diffuse to, without limitation, a single point (i.e., a localized area) of the implant. The single point may provide the entire counterforce by, e.g., leveraging, diffusing, and canceling that occurs at the single counterforce point. Leveraging may include supporting radial movement of the implant, about the single counterforce point acting as a pivot. The radial movement causes a "see-saw" effect in which the external force pushes a portion of the implant in the direction of the external force, and an opposite portion of the implant is moved in the opposite direction. Diffusing the force may include redirecting the force as radial forces that propagate from the single counterforce point and diffuse through the implant. Canceling the diffused forces may include redirecting the forces in a direction that opposes and thereby balances the radial forces diffusing from the external force. The concentration of forces on this single point requires the bone to support these forces across a very small surface area thus making it a single point of failure.

Further, radial forces and/or radial movement (or, "axial compression forces") from the implant may damage areas of the bone structure that are particularly susceptible to weakening and damage. The damage may cause a breakdown of the bone structure, including, e.g., microfractures which heal over time with scar tissue, and trauma of the healthy bone that has sufficiently survived the implant insertion process and is critical to the timeframe and quality of healing.

In view of the above, there is a need for an orthopedic fastener that minimizes trauma and injury to tissues and bone, especially trabecular bone, during orthopedic procedures and prevents fracturing, loosening, or disengaging of the orthopedic fastener over the life of the implant once it is in place. In addition, a need exists to efficiently leverage the natural behavior of bone while distributing the radial forces through the implant after insertion. Further, a need exists to balance, e.g., axial pull-out forces that resist the implant pulling out of the bone and damage from radial forces.

BRIEF DESCRIPTION OF THE EXEMPLARY EMBODIMENTS

For purposes of this disclosure, "orthopedic fastener" generally and without limitation means a device or system for securing, fixing, or attaching bones, tissues, muscles, implanted devices, etc. to a bone or body structure.

In an aspect, the disclosure relates to an orthopedic fastener including a shaft and a plurality of compound parabolic petals. The petals may extend helically around the shaft, and be configured to compress trabecular bone.

In an aspect, the disclosure relates to an orthopedic fastener including a head portion and a shaft. The shaft may include a proximal end, a distal end, and a first force diffusion area positioned at the proximal end of the shaft. The first force diffusion area may be connected to the head portion and extend radially inwardly from the head portion. The orthopedic fastener may further include a plurality of compound parabolic petals, which may extend helically around the shaft. The petals may be configured to compress trabecular bone. The first force diffusion area may be dimensioned for distributing a radial force, towards keystone portions of trabecular bone that are compressed against the first force diffusion area.

In an aspect, the disclosure relates to a method for orthopedic fastening. The method may include, inserting an orthopedic fastener into a bone. The orthopedic fastener may include a shaft and a plurality of compound parabolic petals extending helically around the shaft. The method may further include compressing trabecular bone between the petals, in response to inserting the orthopedic fastener into the bone.

BRIEF DESCRIPTION OF THE FIGURES

A more particular description will be rendered by reference to specific embodiments thereof that are illustrated in the appended drawings. Understanding that these drawings depict only typical embodiments thereof and are not therefore to be considered to be limiting of its scope, exemplary embodiments will be described and explained with additional specificity and detail through the use of the accompanying drawings in which:

FIG. 3A shows a side perspective view of an exemplary 3-petal orthopedic fastener according to the disclosure;

FIG. 3B shows an opposite side perspective of an exemplary 3-petal orthopedic fastener according to the disclosure;

FIG. 7 shows an enlarged view of exemplary compound parabolic petals according to the disclosure;

FIG. 8 shows an enlarged view of exemplary compound parabolic petals according to the disclosure;

FIG. 9A shows a side perspective view of an exemplary 2-petal embodiment of an orthopedic fastener according to the disclosure;

FIG. 9B shows a top perspective view of an exemplary 2-petal embodiment of an orthopedic fastener according to the disclosure;

Figure 1:
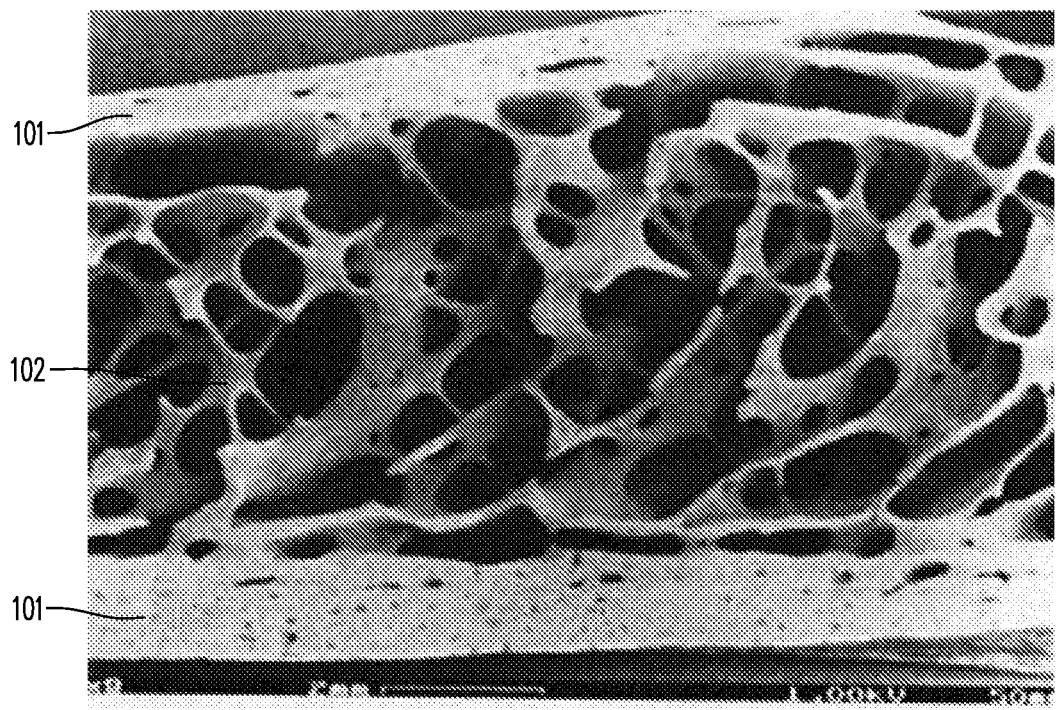
FIG. 1 shows a micrograph of trabecular bone.

Various features, aspects, and advantages of the embodiments will become more apparent from the following detailed description, along with the accompanying figures in which like numerals represent like components throughout the figures and text. The various described features are not necessarily drawn to scale but may be drawn to emphasize specific exemplary features.

The headings used herein are for organizational purposes only and are not meant to limit the scope of the description of the claims. To facilitate understanding, reference numerals have been used, where possible, to designate like elements common to the figures.

DETAILED DESCRIPTION OF THE EXEMPLARY EMBODIMENTS

Reference will now be made in detail to exemplary embodiments of the disclosed devices, systems, and methods. Each example is provided by way of explanation and is not meant as a limitation and does not constitute a definition of all possible embodiments.

Figure 2:
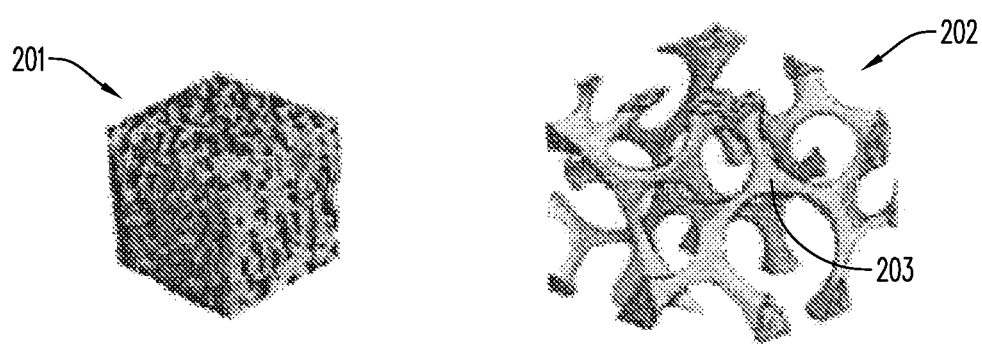
FIG. 2 shows scaled depictions of trabecular bone.

An exemplary orthopedic fastener 300 according to the disclosure is shown in FIG. 3A. The exemplary orthopedic fastener 300 reduces trauma to trabecular bone by, among other things, passing or plowing through interstices between bone material bridges 203 (FIG. 2) instead of piercing, fracturing, or lacerating the trabecular bone, and securing itself in the trabecular bone by compressing the bone material bridges 203 together and in a direction that is both axial along the length of the shaft and perpendicular to the shaft and insertion direction of the orthopedic fastener 300 as described below.

The exemplary orthopedic fastener 300 shown in FIG. 3A includes, among other things, a head portion 301, a tip 302, and a shaft 303 having a proximal end 304 connected to the head portion 301 and a distal end 305 connected to the tip 302 and extending there between. A plurality of petals 306 including petals 306a, 306b, and 306c, discussed further below, are arranged helically around the shaft 303 such that portions of different petals 306 circumferentially overlap along a length L of the shaft 303 and form gaps 540, 550, 560 (explained in detail further below with respect to FIG. 5) between circumferentially overlapping portions of petals 306. The exemplary orthopedic fastener 300 further includes a major diameter 390 and a minor diameter 395. For purposes of this disclosure, the major diameter 390 is the largest diameter at a given point between two lines representing the outline of the orthopedic fastener 300, for example the diameter between the respective crests 391 of two petals 306 located on opposite sides of the shaft 303. This could be, for example and without limitation, a parallel outline, a tapered or conical outline, or a form of a curve similar to the outline of a bullet. In an aspect, an exemplary major diameter range for the exemplary embodiments herein is from approximately 1.8 mm for a small orthopedic fastener used in, e.g., a distal radius of a bone, to 40 mm for a hip, knee, or ankle total joint orthopedic fastener. In an aspect, the major diameter 390 may be tapered to accommodate the specific needs of the application. For example, in a total knee joint orthopedic fastener, the major diameter may have a taper between approximately 0 degrees and 20 degrees The minor diameter 395 is the distance between the respective roots 396 of two petals 306 located on opposite sides of the shaft 303. An exemplary minor diameter 395 range for the shaft 303 in this application is from approximately 1.2 mm for a small orthopedic fastener used in, e.g., a distal radius of a bone, to 25 mm for a hip, knee, or ankle total joint orthopedic fastener.

Figure 5:
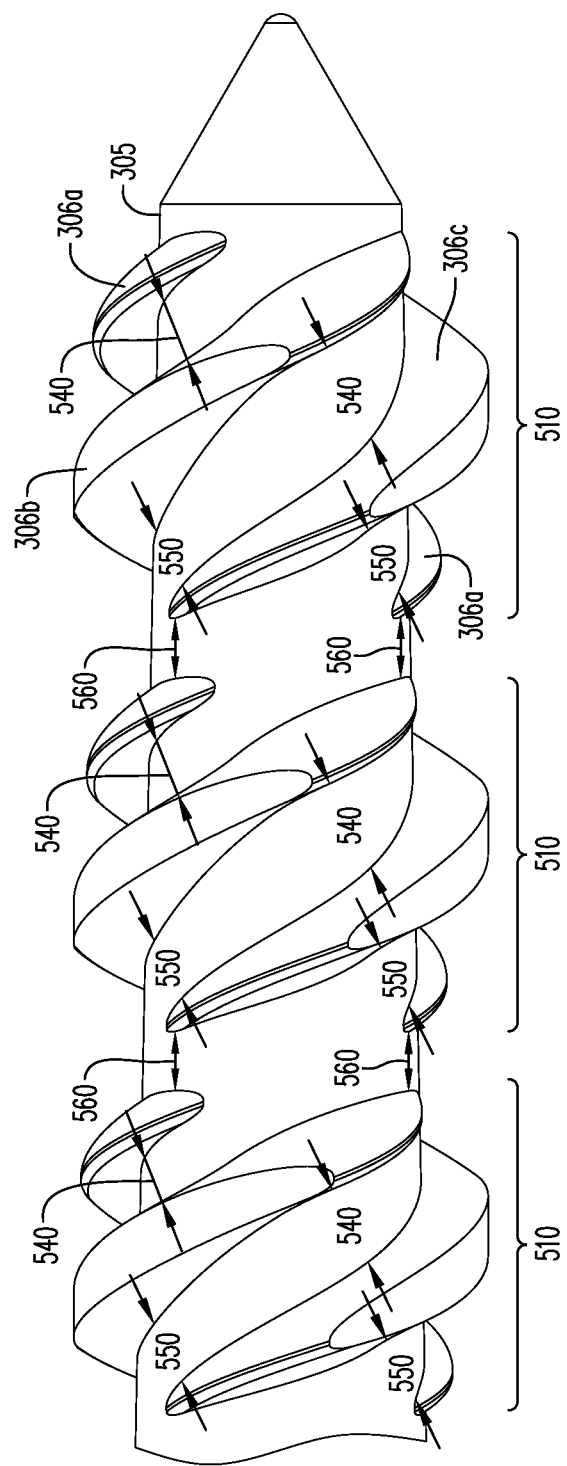
FIG. 5 shows an enlarged view of a portion of an exemplary 3-petal orthopedic fastener according to the disclosure.
Figure 6:
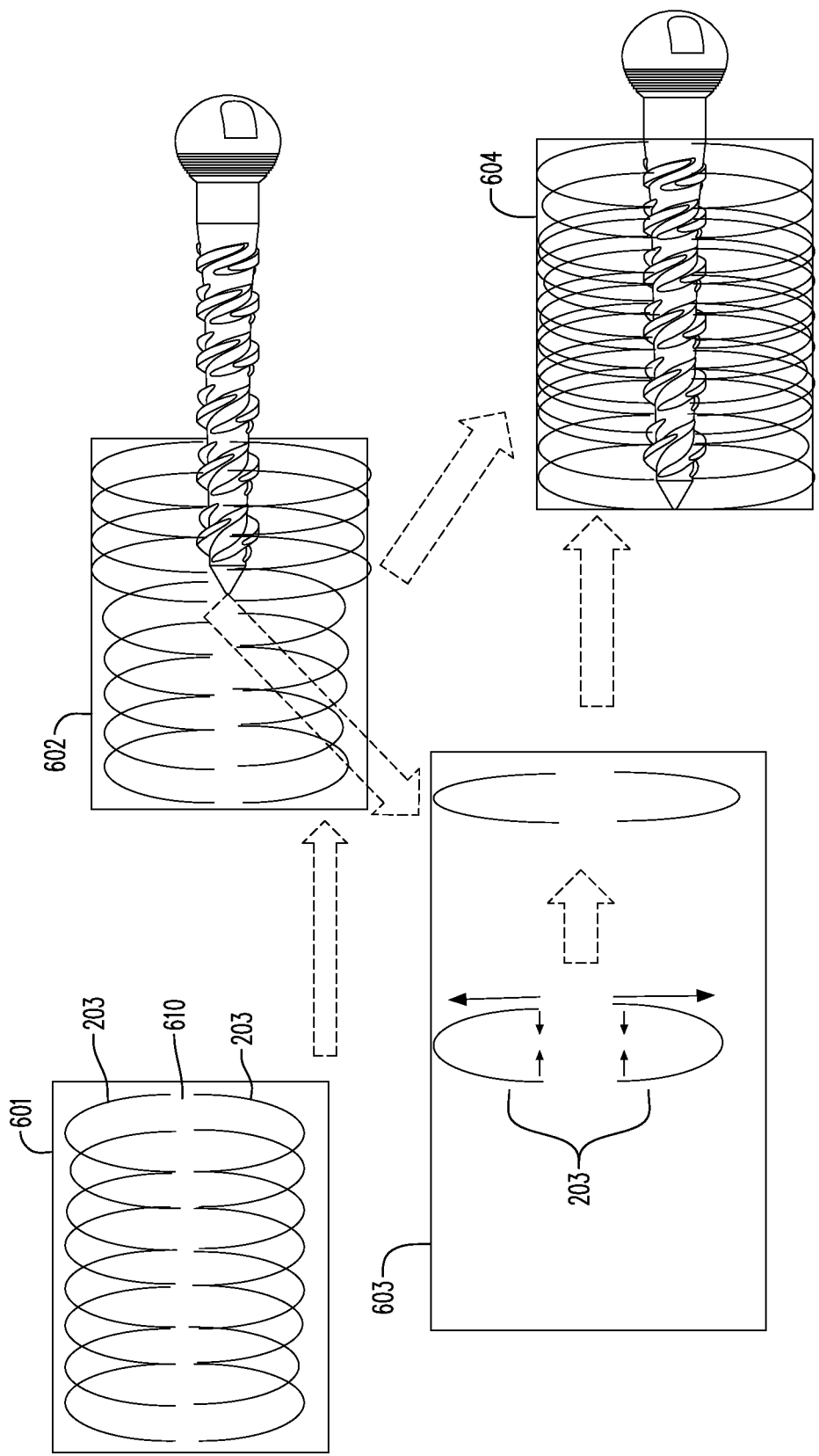
FIG. 6 shows compression of trabecular bone by an exemplary orthopedic fastener according to the disclosure.

The helical configuration of the petals 306 compresses trabecular bone in gaps 540 (FIG. 5) and in a direction perpendicular to the insertion direction of the orthopedic fastener 300 as described with respect to FIG. 6. The petals 306 have a compound parabolic configuration as described further below with respect to, for example, FIG. 7. Thus, for purposes of this disclosure, the phrases "petal(s)" or "blades" and "compound parabolic petal(s)" are interchangeable and refer to the exemplary disclosed embodiments of a compound parabolic petal.

Figure 3C:
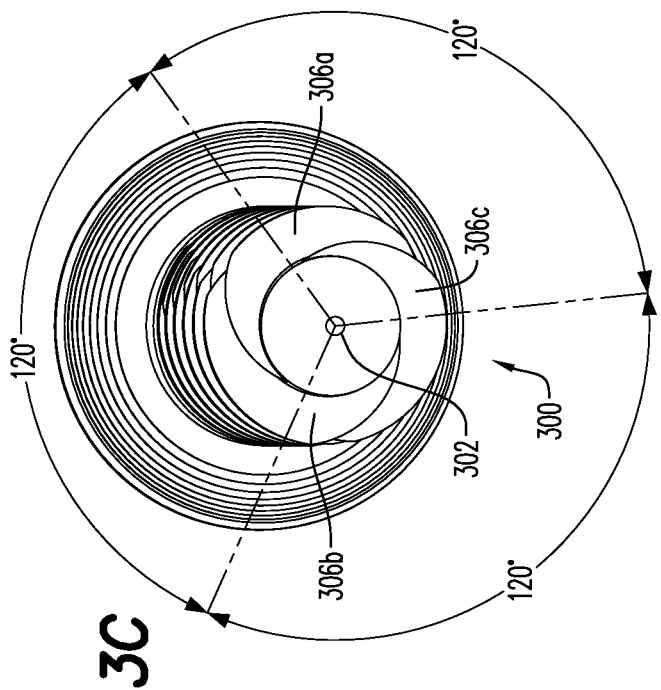
FIG. 3C shows a front plan view of an exemplary 3-petal orthopedic fastener according to the disclosure.

The exemplary helical configuration of the petals 306 and representative petals 306a, 306b, and 306c shown in FIG. 3A is further illustrated in the different perspective views of FIGS. 3B and 3C. FIGS. 3A-3C in conjunction show the exemplary helical configuration around the circumference of the shaft 303. As shown in FIG. 3A and with reference in a direction from the distal end 305 towards the proximal end 304 of the shaft 303, petal 306a begins in the view of FIG. 3A, wraps out of view behind the shaft 303, and continues to wrap around the shaft 303 and ends back in the view of FIG. 3A. Petal 306b begins and ends behind the shaft out of the view of FIG. 3A which shows an intermediate portion of the petal 306b wrapping around the shaft 303 from its beginning to its end. Petal 306c begins behind the shaft out of view of FIG. 3A, wraps around the shaft 303, and ends in the view of FIG. 3A.

FIG. 3B shows a view behind the shaft 303 from the view of FIG. 3A and the corresponding helical configuration of the petals 306, including petals 306a, 306b, and 306c, that is out of the view of FIG. 3A. For example, FIG. 3B shows an intermediate portion of petal 306a wrapping around the shaft 303 from its beginning to its end which are shown in FIG. 3A. Further, the beginning and end of petal 306b, not visible in FIG. 3A, are shown in FIG. 3B. Petal 306b begins in the view of FIG. 3b, wraps out of view to the intermediate portion shown in FIG. 3A, and continues to wrap around the shaft 303 and ends back in the view of FIG. 3B. In addition, FIG. 3B shows the beginning of petal 306c which wraps around the shaft 303 to its end shown in FIG. 3A.

FIGS. 3A and 3B illustrate the overlapping configuration of the petals 306 in an exemplary embodiment. With continuing reference to the view shown in FIG. 3A and in a direction from the distal end 305 to the proximal end 304 of the shaft 303, petal 306a begins closest (as between petals 306a, 306b, and 306c) to the distal end 305, overlaps petals 306b and 306c, and ends farthest from the distal end 305. On the other hand, in the view of FIG. 3B petal 306b begins closest to the distal end 305, overlaps petals 306c and 306a, and ends farthest from the distal end 305 in the view of FIG. 3B. This overlapping helical configuration of the petals 306 contributes to the exemplary disclosed compression of trabecular bone. As discussed further below with respect to FIG. 5, the arrangement of representative petals 306a-306c constitutes a repeating set (e.g., 510) of three petals that is repeated along the length L of the shaft 303 in the exemplary embodiment.

FIG. 3C shows the exemplary orthopedic fastener 300 shown in FIGS. 3A and 3B from the perspective along the tip 302. As shown in FIG. 3C, the exemplary helical configuration of petals 306, by reference to representative petals 306a, 306b, and 306c, is also achieved in part by spacing the beginning and ends of successive petals 306a, 306b, 306c at 120 degrees apart around the circumference of the shaft 303. In other embodiments the petals 306 may be spaced at whatever interval is required for a particular application consistent with this disclosure.

Figure 4:
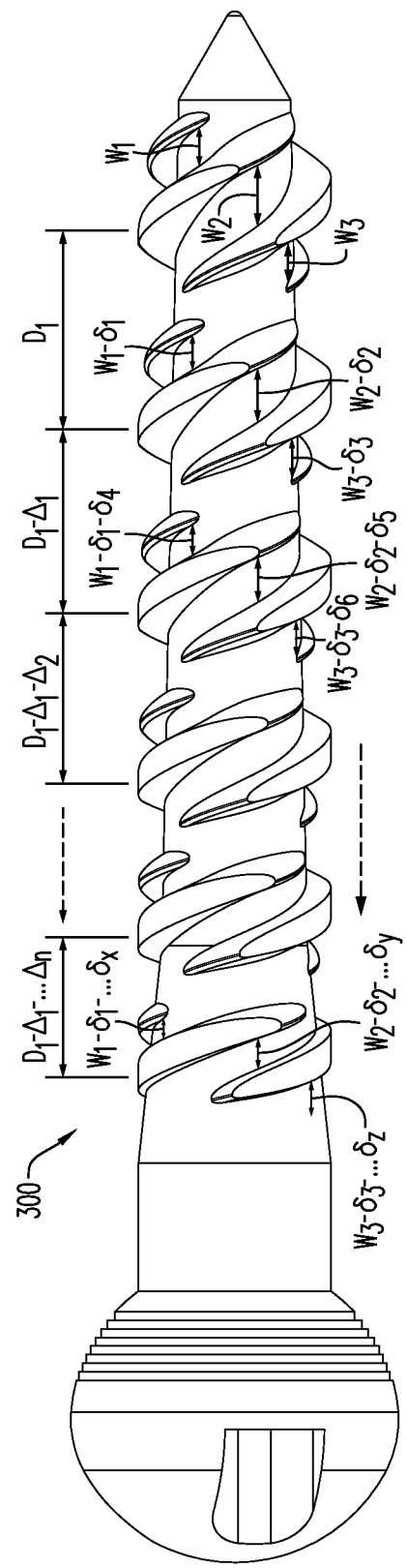
FIG. 4 shows a side perspective view of an exemplary 3-petal orthopedic fastener with general dimensions according to the disclosure.

Other dimensional aspects of the exemplary disclosed embodiment of an orthopedic fastener 300 shown in FIGS. 3A-3C are shown in FIG. 4. As shown in FIG. 4, and with continuing reference to FIG. 3A, the exemplary embodiment includes at least one distance, e.g., $D_1$, between successive petals 306 along the same circumferential angle on the shaft 303 and widths $W_1$-$W_3$ between petals 306. In one aspect of the exemplary embodiment shown in FIG. 4, the distance between petals 306 progressively decreases in a direction from the distal end 305 to the proximal end 304. Accordingly, the distance between successive petals 306 along the same circumferential angle on the shaft 303 will progressively decrease from $D_1$, to $D_1$-$\Delta_1$, to $D_1$-$\Delta_1$-$\Delta_2$, and through to $D_1$-$\Delta_1$-...$\Delta_n$, where $\Delta_1, \Delta_2, \ldots$ and $\Delta_n$ can be any suitable value depending on the particular application and requirements for the orthopedic fastener 300. Similarly, the widths $W_1$-$W_3$ between petals 306 will decrease respectively from $W_1, W_2$, and $W_3$, to $W_1$-$\delta_1$, $W_2$-$\delta_2$, and $W_3$-$\delta_3$, to $W_1$-$\delta_1$-$\delta_4$, $W_2$-$\delta_2$-$\delta_5$, and $W_3$-$\delta_3$-$\delta_6$, through to $W_1$-$\delta_1$-$\delta_x$, $W_2$-$\delta_2$-$\delta_y$, and $W_3$-$\delta_3$-$\delta_z$, where $\delta_1, \delta_2, \ldots \delta_z$ can be any suitable value depending on the particular application and requirements for the orthopedic fastener 300.

In the exemplary disclosed embodiments, the range of distances ($D_1$, etc.) between successive petals 306 along the same circumferential angle of the shaft 303, including on the same orthopedic fastener 300 with progressive dimensions as discussed above, may be from approximately 1.5 mm to about 15 mm. The range of widths ($W_1$, etc.) between directly adjacent petals 306 may be from approximately 0.5 mm to about 7.5 mm, and the range of petal heights h (see FIG. 7) may be from approximately 0.1 mm to about 12.5 mm. The exemplary dimensions are not meant to limit the scope of the disclosure and the range(s) of dimensions may accommodate for, among other things, the needs in the design of a total joint orthopedic fastener. The actual dimensions may vary widely depending upon factors including but not limited to the density, rigidity, and liquid content of the trabecular bone at the fixation site, the degree of trabecular bone compression sought between successive petals, and the ratio of the major diameter 390 to the minor diameter 395 of a particular orthopedic fastener for fixation in a particular bone (because of additional radial compression not just from the standpoint of axial compression along the length of the cells, but the compression of the trabecular bone from the conical cross-section of the minor diameter 395 against the cortical walls (see FIG. 6)—i.e., the conical cross-section of the minor diameter 395 allows compression of the trabecular bone against the cortical walls wherein a bigger (diameter) shaft squeezes the trabecular bone further toward the cortical walls). Other factors for dimensioning the exemplary orthopedic fastener (e.g., 300) that affect the above considerations and others involve, for example and without limitation, the bone or region (i.e., spinal, facial, total joint, etc.) for fixation, the age/development of the patient, the forces that are likely to act on the fastener, etc.

Other dimensions that will vary depending on the size of the bone, application, patient, injury, forces acting on the orthopedic fastener, etc. are the circumferential length of the petals 306 extending around the shaft, the length L of the shaft, and the minor diameter 395, as explained further below with respect to certain exemplary embodiments.

By way of example, in areas such as the thoracic-lumbar region, trabecular bone is relatively denser and harder given that it has to support more weight from the rest of the spine, head, neck, and other forces above it. Here, the fastener must anchor itself into the medium of the insertion point with maximum strength while taking into consideration the limiting factors such as dimensional spaces available to the anchoring devices. For example, the insertion point is typically through the pedicle canal, which, due to its size, limits the available diameter for orthopedic fasteners. This limiting factor requires an anchoring device that resists axial (pullout) as well as radial and in some cases torsional (within the medium) forces. In an aspect, changes in bone density may require a modification to the dimensions and spacing of the petals. Understanding the environment, the appropriate orthopedic fastener is capable both of withstanding the relevant forces over the lifetime of the patient while maximizing anchoring stability in either omni-directional or bi-directional configurations at a surgeon's discretion depending upon, e.g., the patient, the patient's age, the nature of the injury, bone health etc.

Another objective of the orthopedic fastener is to minimize trauma to the trabecular bone and reduce healing time. Accordingly, an orthopedic fastener may have, for example, a 3-petal design (as previously discussed for omni-directional stability) with relatively shorter distances between petals to fit dense, hard, trabecular bone. For example, in the exemplary disclosed orthopedic fastener 300, application(s) for lumbar fixation may include a range of distances between successive petals 306 along the same circumferential angle of the shaft 303 from approximately 4 mm to about 2.5 mm and a width between successive, adjacent petals 306 of approximately 1 mm. The height h range of the petals in this exemplary orthopedic fastener may be from approximately 0.2 mm to about 1.0 mm. The exemplary circumferential lengths of petals 306 extending around the shaft may be from a range of approximately 5 mm to 6.5 mm, and the length L range of the shaft may be approximately 6 mm to 150 mm. In the exemplary disclosed embodiment shown in FIGS. 3A-3C, the shaft is approximately 30 mm long. A more particular minor diameter range for the exemplary examples herein is from approximately 2.6 mm to 4 mm.

As further detailed with respect to FIG. 6, the orthopedic fastener 300 compresses the trabecular bone bridges (203) towards each other and in a direction perpendicular to the insertion direction of the orthopedic fastener 300. The trabecular bone cell size and density in the cervical and lumbar spine (discussed further below with respect to FIGS. 9A-10) are particularly well suited to the compression dynamics created by the disclosed orthopedic fastener 300 (900, FIG. 9A) for securing the orthopedic fastener 300 and avoiding trauma to the trabecular bone. Further, the insertion point for an orthopedic fastener in cervical and lumbar spinal fixation procedures is already perpendicular to the forces acting on the bone and the orthopedic fastener interacts with the natural trabecular bone structure substantially according to the exemplary compression dynamics described herein. For example, an orthopedic fastener in cervical and lumbar fixation procedures may pass along the base of the trabecular bone materials bridges 203 as opposed to penetrating through the bridges 203. For at least the above reasons, the exemplary disclosed orthopedic fastener 300 achieves a substantial degree of compression in both radial and axial directions of the cervical and lumbar spine and securement therein.

Progressively decreasing the distance between petals 306 progressively increases the amount of trabecular bone compression that the orthopedic fastener 300 generates as it advances through the trabecular bone and helps to distribute the compressive forces along the length L of the orthopedic fastener 300/shaft 303. For example, the leading tip 302 and distal end 305 of the orthopedic fastener 300 encounter and compress more trabecular bone than the proximal end 304 as the orthopedic fastener 300 travels through the trabecular bone. Decreasing the distance between petals 306 from the distal end 305 to the proximal end 304 compensates for the difference between the amount of trabecular bone encountered and compressed between the distal end 305 and the proximal end 304 and distributes compressive forces along the length L of the orthopedic fastener 300/shaft 303. Distributing the compressive forces along the length L of the orthopedic fastener 300/shaft 303 enhances securement of the orthopedic fastener 300.

The exemplary embodiment shown in FIGS. 3A-4 also includes a shaft 303 that tapers in a direction from the proximal end 304 to the distal end 305 to increase the amount of compression generated by the orthopedic fastener 300 and distribute compressive forces along the length L of the orthopedic fastener 300/shaft 303. As the exemplary orthopedic fastener 300 is advanced through trabecular bone, the increasing diameter of the shaft 303 coupled with the axial compressive characteristics of the design provides progressively increasing compression of the trabecular bone between the orthopedic fastener 300 and, e.g., the cortical walls. In the exemplary embodiment shown in FIGS. 3A-4, the shaft 303 is formed integrally with the head portion 301 and tip 302. In other embodiments, one or more of the shaft 303, head portion 301, and tip 302 may be separate components joined by welding, adhesive, or other known techniques.

The exemplary embodiment shown in FIGS. 3A-4 also includes a connecting bulb 308 connected to the head portion 301. The connecting bulb 308 connects to additional components of an orthopedic fastening system described further below with respect to FIG. 11. In other embodiments, the head portion 301 may take any form consistent with this disclosure. For example, head portion 301 may be attached to a variety of connectors for particular surgical systems or head portion 301 may be the connector for other components or surgical systems. Head portion 301 may also be integral with the shaft 303 and/or refer simply to the terminus of the shaft 303.

The tip 302 in the exemplary embodiment shown in FIGS. 3A-4 is cone-shaped. In other embodiments the tip 302 may be any shape capable of passing through trabecular bone. The orthopedic fastener 300 and/or particular features, such as tip 302, in the exemplary embodiment shown in FIGS. 3A-4 may be formed from any materials with sufficient strength, hardness, and other properties for the applications in which the orthopedic fastener 300 is used. Exemplary materials are those allowed by the FDA for permanent medical implants such as cobalt, chrome, and titanium and compounds thereof. The orthopedic fastener 300 including petals 306 and other features may be machined from a single piece of such material, molded by injection molding or other known techniques, assembled by joining different components by welding, adhesives, etc., or by any other process that meets particular objectives (such as practicality, cost, dimensional tolerances, etc.) and is consistent with the scope of this disclosure.

With reference now to FIG. 5, the configuration of petals 306 and gaps 540, 550, 560 in the exemplary orthopedic fastener 300 shown in FIGS. 3A-4 is illustrated in additional detail. As shown in FIG. 5, petals 306 in the exemplary embodiment are arranged in repeating sets 510 of three petals 306 (e.g., 306a, 306b, 306c). Repeating sets 510 are representatively shown in the blown-up view of the distal end 305 in FIG. 5 and it is understood that such repeating sets continue up the shaft 303 to the proximal end 304 as in the exemplary embodiment shown in FIGS. 3A-4.

The gaps 540, 550, 560 between petals 306 include compressive gaps 540, expansive gaps 550, and transition gaps 560. Compressive gaps 540 are created in part by undercut parabolic portions 701 of the petals 306 as described with respect to FIG. 7. The undercut and/or concave parabolic portions "scoop" and compress trabecular bone in the compressive gaps 540 as the orthopedic fastener 300 is turned and advanced through the trabecular bone in a similar fashion as a cupped hand scoops and compresses dirt while digging. For example, with reference to FIGS. 2 and 6, the orthopedic fastener 300 in use is, to the extent possible, passed along the base 610 of bridges of trabecular bone material 203. Before the orthopedic fastener 300 is inserted (shown in FIG. 6 as state 601), the bridges of trabecular bone material 203 are uncompressed. As the orthopedic fastener 300 is inserted (FIG. 6, state 602), the bridges of trabecular bone material 203 are compressed inwards and in a direction perpendicular to the insertion direction of the orthopedic fastener 300 (see arrows in detail 603) by compressive gaps 540. When the orthopedic fastener 300 is fully inserted (FIG. 6, state 604), the trabecular bone is compressed between the orthopedic fastener 300 and the cortical wall along the length of the orthopedic fastener 300, thus securing the orthopedic fastener 300.

Expansive gaps 550 are created in part by overcut parabolic portions 702 of the petals 306 as described with respect to FIG. 7. The expansive gaps 550 release a portion of the compression that the compressive gaps 540 create on the trabecular bone while maintaining some compression on the trabecular bone as the orthopedic fastener 300 is turned and advanced through the trabecular bone. Systematically releasing a portion of the compression reduces resistance against further compression of the trabecular bone and enhances uniformity of the compression along the length of the orthopedic fastener 300. For example, applying constant compression from an orthopedic fastener advancing through trabecular bone may compact the trabecular bone in one region such as the distal end of the orthopedic fastener. Compacting the trabecular bone in one region may increase the amount of force needed to further advance the orthopedic fastener, and thereby increase the risk of damage to the trabecular bone, and result in imbalanced compression at different points along the length of the orthopedic fastener.

Transition gaps 560 are areas between repeating sets 510 of petals 306 where compressed trabecular bone passes from one repeating set to a following repeating set. Transition gaps 560 maintain most of the compression created in the previous repeating set such that the trabecular bone may be further compressed in the successive repeating set. In the exemplary embodiment and sections thereof shown in FIGS. 3A-5, the length of successive repeating sets 510 decreases in a direction from the distal end 305 to the proximal end 304 as the distance between the petals 306 decreases as previously described. Accordingly, overall compression can be increased in each successive repeating set 510.

In the exemplary orthopedic fastener 300 and sections thereof shown in FIGS. 3A-5, each of the three petals 306 in each repeating set 510 has at least one compressive gap 540 and one expansive gap 550. Thus, with each full, 360 degree turn of the orthopedic fastener 300 during advancement, three cycles of compression and partial release is achieved for every repeating set 510 of petals 306 that is within the trabecular bone. Accordingly, in an exemplary method of orthopedic fastening trabecular bone is progressively compressed in this compress-partial release-compress fashion using an orthopedic fastener such as the exemplary orthopedic fastener 300 and features thereof shown in FIGS. 3A-5. The configuration of each petal 306 including the compressive gap 540 and expansive gap 550 is shown in further detail and described with respect to FIGS. 7 and 8.

With reference now to FIG. 7, a detailed view of an exemplary embodiment of petals, i.e., compound parabolic petals 306, is shown. Petals 306 project away from the shaft 303 in the height direction h and have a compound parabolic configuration. For purposes of the disclosure, a "compound parabolic petal" means a petal configured with a plurality of parabolic features including continuous parabolic structures and/or transitions such as those shown in FIG. 7 and described with respect thereto. The height h of compound parabolic petals 306 can be any suitable value depending on the particular application and requirements for an orthopedic fastener. Moreover, it could be modified to accommodate the variances in bone structure found in different medical conditions that are not optimal such as bone that has been compromised by Cancer or Tuberculosis as an example.

The compound parabolic structure of the petals 306 is also chosen to suit the particular application and requirements for an orthopedic fastener. With reference to the exemplary compound parabolic petal 306 shown in FIGS. 7 and 8, each petal 306 includes one proximal parabola 700 shifting from an undercut 701 to an overcut 702 parabolic aspect on a proximal side 780 (i.e., facing the proximal end 304 of shaft 303) and a lateral parabolic aspect 707 in a direction lateral to the minor diameter 395. The proximal parabola 700 creates the compressive gap 540 and expansive gap 550 respectively between the undercut 701 and overcut 702 parabolic aspects and an adjacent petal 306. Thus, as the orthopedic fastener 300 is turned and advanced through trabecular bone each compound parabolic petal 306 transitions from compressing the trabecular bone to releasing a portion of the compression creating the exemplary compress-partial release-compress progression.

The undercut 701 and overcut 702 parabolic aspects also have respective closed 704 and open 705 lateral parabolic aspects 707. The closed parabolic aspect 704 contributes to compression of trabecular bone by extending in towards the undercut parabolic aspect 701 to contain the trabecular bone in the undercut parabolic aspect 701. The open parabolic aspect 705 contributes to expansion of trabecular bone by extending away from the overcut parabolic aspect 702 to open additional space in the overcut parabolic aspect 702. Line x illustrates a contour of the proximal side 780 of the petal 306 representing geometrical radii along the length L of the shaft 300 from a leading edge 715 of the petal 306 to a trailing edge 716 (not visible on the other side of the shaft) of the petal 306. The contour x enhances axial compression of the trabecular bone along the shaft and thereby enhances radial compression of the trabecular bone 102 against the cortical wall 101.

With continuing reference to FIG. 7, each petal 306 has an arc (or, "capped") crest 708 extending between the proximal 780 and a distal 790 (i.e., facing the distal end 305 of shaft 303, as shown in FIG. 8) side of the petal 306. In the exemplary embodiment shown in FIG. 7, the arc crest 708 is parabolic along its length. Transition between the distal face 790 and the proximal face 780 of the petal 306 is via compound parabolic radii or aspects 705, 706 along each side of the arc crest 708 extending respectively into the overcut, open parabolic aspects 801, 802 (FIG. 8) of the distal side 790 and the undercut, closed parabolic aspect 701 and overcut, open parabolic aspect 702 of the proximal side 780. The compound parabolic radii or aspects 705, 706 allow for smooth transitions between the distal 790 and proximal 780 sides and reduces the occurrence of sharp edges.

With reference now to FIG. 8, the distal side 790 of the petal transitions from an open, overcut parabolic aspect 801 to a reduced overcut parabolic aspect 802. The open, overcut parabolic aspect 801 of the distal side 790 is configured adjacent to the open, overcut aspect 702 of the proximal side 780 of an adjacent petal 306. The reduced overcut parabolic aspect 802 is configured adjacent to the closed, undercut parabolic aspect 701 of the proximal side 780 of an adjacent petal 306. The gaps between respective portions of the proximal 780 and distal 790 sides of adjacent petals 306 form the compressive 540 and expansive 550 gaps.

Figures 9C, 9D:
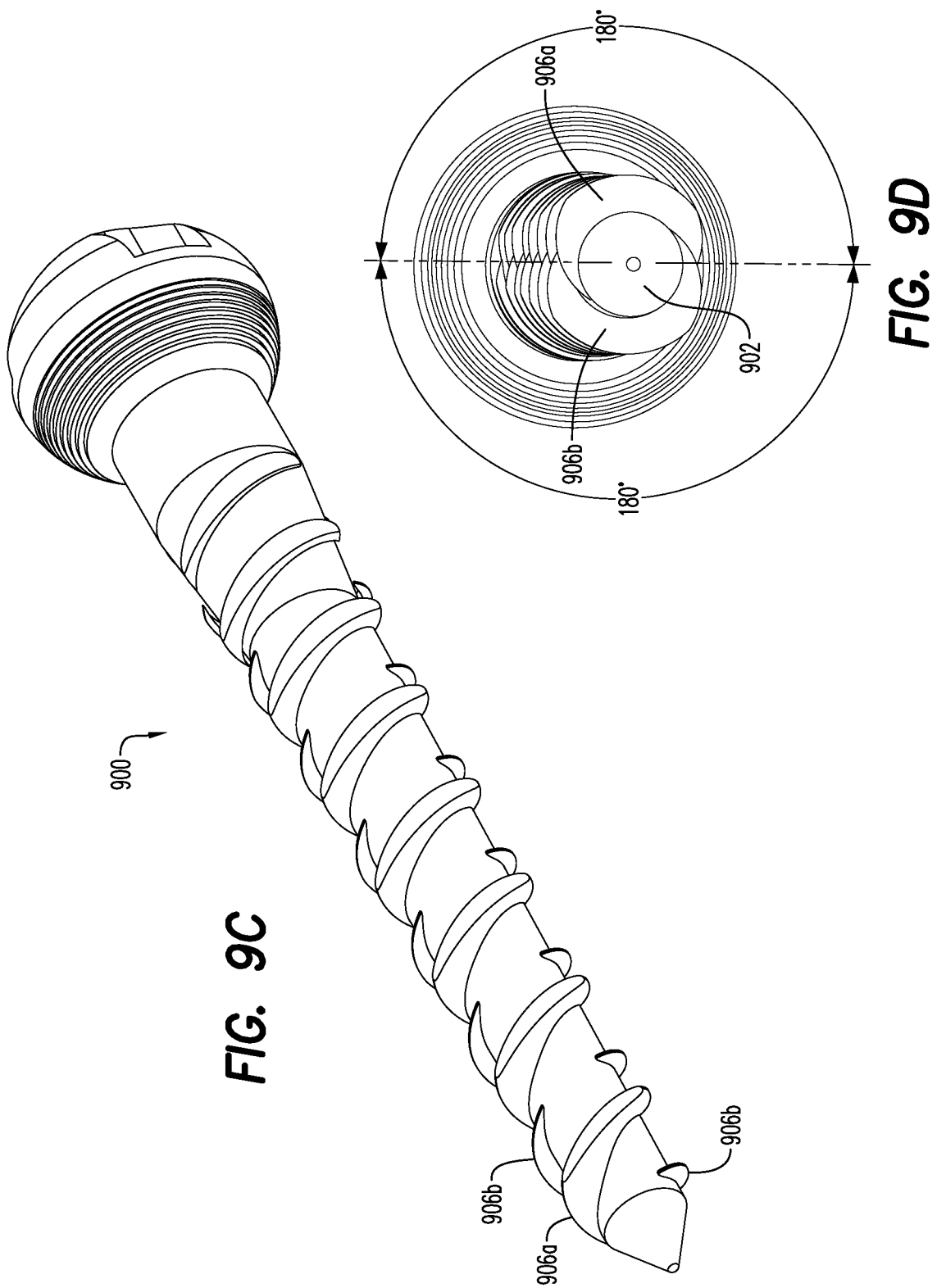
FIG. 9C shown an opposite top perspective view of an exemplary 2-petal embodiment of an orthopedic fastener according to the disclosure.
FIG. 9D shows a front plan view of an exemplary 2-petal embodiment of an orthopedic fastener according to the disclosure.
Figure 9E:
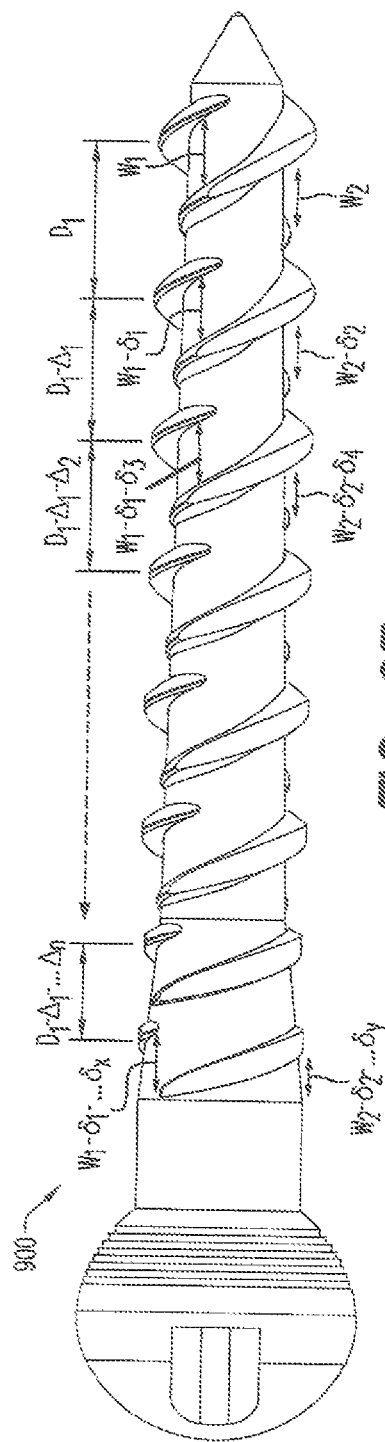
FIG. 9E shows a side perspective view of an exemplary 2-petal embodiment of the orthopedic fastener with general dimensions.
Figure 10:
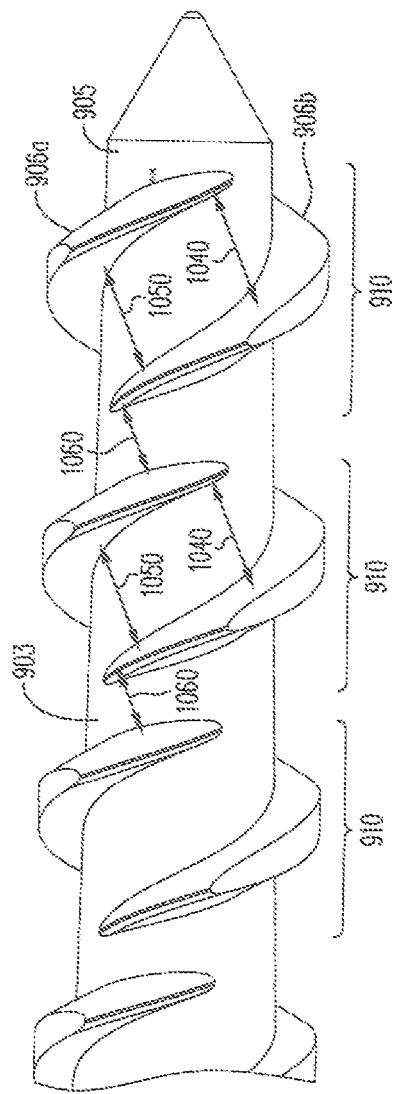
FIG. 10 shows an enlarged view of exemplary compound parabolic petals in an exemplary 2-petal embodiment of the orthopedic fastener according to the disclosure.

With reference now to FIGS. 9A-10, an exemplary embodiment of an orthopedic fastener 900 having repeating sets 910 of two petals is shown. With reference to FIG. 9A, the exemplary orthopedic fastener 900 includes, among other things, a head portion 901, a tip 902, and a shaft 903 having a proximal end 904 connected to the head portion 901 and a distal end 905 connected to the tip 902 and extending therebetween. A connecting bulb 908 is connected to the head portion 901 and connects to additional components of an orthopedic fastening system such as the one shown in FIG. 11. A plurality of petals 906 including petals 906a, 906b, discussed further below, are arranged helically around the shaft 903 such that portions of different petals 906 circumferentially overlap along a length L of the shaft 903 and form gaps 1040, 1050, 1060 (explained in detail further below with respect to FIG. 10) between circumferentially overlapping portions of petals 906. The general configuration, variations, and operation of the two-petal fastener 900 follows the three-petal fastener 300 described above with respect to FIGS. 3A-3C, except that the two-petal fastener 900 has repeating sets 910 of two petals instead of three.

The exemplary helical configuration of the petals 906 and representative petals 906a and 906b are shown in the various perspective views of FIGS. 9A-9D. FIGS. 9A and 9B respectively show plan and top perspective views from the same side of the orthopedic fastener 900. FIG. 9C shows a top perspective view of the orthopedic fastener 900 from an opposite, or back side to that shown in FIGS. 9A and 9B. Petal 906a begins in the views of FIGS. 9A and 9B, wraps around the shaft as shown in FIG. 9C, and ends back in the view of FIG. 9A. Petal 906b begins in the view of FIG. 9C, wraps around the shaft as shown in FIGS. 9A and 9B, and ends in the views of both FIGS. 9B and 9C. FIGS. 9A-9C illustrate the overlapping configuration of the petals 906 in an exemplary embodiment. With continuing reference to the view shown in FIG. 9A and in a direction from the distal end 905 to the proximal end 904 of the shaft 903, petal 906a begins closest (as between petals 906a and 906b) to the distal end 905. On the other hand, in the view of FIG. 9C petal 906b begins closes to the distal end 905, overlaps petal 906a as shown in the views of FIGS. 9A and 9B, and ends farthest from the distal end 905 in the view of FIG. 9C. This overlapping helical configuration of the petals 906 contributes to the exemplary disclosed compression of trabecular bone. As shown in FIG. 9A, the arrangement of representative petals 906a and 906b constitutes a repeating set 910 of two petals that is repeated along the length L of the shaft 903 in the exemplary embodiment.

FIG. 9D shows the exemplary orthopedic fastener 900 shown in FIGS. 9A-9C from the perspective along the tip 902. The exemplary helical configuration of petals 906, by reference to representative petals 906a and 906b, is also achieved in part by spacing the beginning and ends of successive petals (e.g., 906a and 906b) at 180 degrees apart around the circumference of shaft 903.

Other dimensional aspects of the exemplary disclosed embodiment of an orthopedic fastener 900 shown in FIGS. 9A-9D are shown in FIG. 9E. As shown in FIG. 9E, and with continuing reference to FIG. 9A, the exemplary embodiment includes at least one distance, e.g., $D_1$, between successive petals 906 along the same circumferential angle on the shaft 903 and widths $W_1$-$W_2$ between petals 906. In one aspect of the exemplary embodiment shown in FIG. 9E, the distance between petals 906 progressively decreases in a direction from the distal end 905 to the proximal end 904. Accordingly, the distance between successive petals 906 along the same circumferential angle on the shaft 903 will progressively decrease from $D_1$, to $D_1$-$\Delta_1$, to $D_1$-$\Delta_1$-$\Delta_2$, and through to $D_1$-$\Delta_1$-...$\Delta_n$, where $\Delta_1$, $\Delta_2$, ... and $\Delta_1$ can be any suitable value depending on the particular application and requirements for the orthopedic fastener 900. Similarly, the widths $W_1$ and $W_2$ between petals 906 will decrease respectively from $W_1$ and $W_2$ to $W_1$-$\delta_1$ and $W_2$-$\delta_2$, to $W_1$-$\delta_1$-$\delta_3$ and $W_2$-$\delta_2$-$\delta_4$, through to $W_1$-$\delta_1$-$\delta_x$ and $W_2$-$\delta_2$-$\delta_y$, where $\delta_1$, $\delta_2$, ... $\delta_y$ can be any suitable value depending on the particular application and requirements for the orthopedic fastener 900.

The exemplary two-petal fastener 900 may find application, by way of example, in cervical fixation procedures. Trabecular bone in the cervical spine is typically softer and spongier to support the head and neck and movement. Thus, distances between successive petals 906 along the same circumferential angle on the shaft 903 ($D_1$, etc.) may tend to be short as less distance is needed to achieve required compression. In the exemplary two-petal fastener 900, exemplary ranges of distances ($D_1$, etc.) between successive petals 906 along the same circumferential angle on the shaft 903 are from approximately 3 mm to about 1.5 mm. An exemplary width ($W_1$, etc.) between successive, adjacent petals 906 is approximately 1 mm and an exemplary range of heights h of petals is from approximately 0.15 mm to 1 mm. An exemplary range for the circumferential length of the petals 906 around the shaft 903 is from approximately 7 mm-10 mm and an exemplary range for the minor diameter of the shaft is approximately 2.5 mm-4.5 mm. An exemplary range for the shaft length L is approximately 6 mm-150 mm, and in the exemplary disclosed embodiment the shaft length is approximately 30 mm.

With reference now to FIG. 10, the configuration of petals 906 and gaps 1040, 1050, 1060 in the exemplary orthopedic fastener 900 shown in FIGS. 9A-9E is illustrated in additional detail. As shown in FIGS. 9A and 10, petals 906 in the exemplary embodiment are arranged in repeating sets 910 of two petals (e.g., 906a and 906b). Repeating sets 910 are representatively shown in the blown-up view of the distal end 905 in FIG. 10 and it is understood that such repeating sets continue up the shaft 903 to the proximal end 904 as in the exemplary embodiment shown in FIGS. 9A-10. The petals 906 are compound parabolic petals having a similar configuration as previously described with respect to FIG. 7.

The gaps 1040, 1050, 1060 between petals 906 include compressive gaps 1040, expansive gaps 1050, and transition gaps 1060. Similar to the exemplary three-petal orthopedic fastener 300 shown in FIGS. 3A-5, compressive gaps 1040 are created in part by undercut parabolic portions 701 (FIG. 7) of the petals 906. The undercut parabolic portions 701 "scoop" and compress trabecular bone in the compressive gaps 1040 as the orthopedic fastener 900 is turned and advanced through the trabecular bone in a manner as previously described with respect to the exemplary three-petal orthopedic fastener 300 and with reference to FIGS. 2 and 6. Expansive gaps 1050 are created in part by overcut parabolic portions 702 (FIG. 7) of the petals 906 in the manner described with respect to the exemplary three-petal orthopedic fastener 300. The expansive gaps 1050 release a portion of the compression that the compressive gaps 1040 create on the trabecular bone while maintaining some compression on the trabecular bone as the orthopedic fastener 900 is turned and advanced through the trabecular bone. Transition gaps 1060 are areas between repeating sets 910 of petals 906 where compressed trabecular bone passes from one repeating set to a following repeating set. Transition gaps 1060 maintain most of the compression created in the previous repeating set such that the trabecular bone may be further compressed in the successive repeating set. In the exemplary orthopedic fastener 900 and sections thereof shown in FIGS. 9A-10, the length of successive repeating sets 910 decreases in a direction from the distal end 905 to the proximal end 904 as the distance between the petals 906 decreases as previously described. Accordingly, overall compression can be increased in each successive repeating set 910.

In the exemplary orthopedic fastener 900 and sections thereof shown in FIGS. 9A-10, each of the petals 906 in each repeating set 910 has at least one compressive gap 1040 and one expansive gap 1050. Thus, with each full, 360 degree turn of the orthopedic fastener 900 during advancement, two cycles of compression and partial release is achieved for every repeating set 910 of petals that is within the trabecular bone. Accordingly, in an exemplary method of orthopedic fastening, trabecular bone is progressively compressed in this compress-partial release-compress fashion using an orthopedic fastener such as the exemplary orthopedic fastener 900 and features thereof shown in FIGS. 9A-10.

The exemplary two-petal orthopedic fastener 900 will generally not achieve the same amount of trabecular bone compression as the exemplary three-petal orthopedic fastener 300 because there is one less stage of compression in each repeating set 910 of petals 906. Further, the exemplary three-petal fastener 300 provides enhanced omnidirectional stability, where multi-directional forces may impact the attachment. On the other hand, the exemplary two-petal fastener 900 provides enhanced bi-directional stability for attachments in areas such as the length of the spine, where forces are concentrated in a finite number of directions such as up and down.

In other embodiments, an orthopedic fastener according to the disclosure may have repeating sets of any number of petals depending on, e.g., the desired application and manufacturing capabilities. Similarly, in general, an orthopedic fastener according to the disclosure may have any number of repeating sets, or none. For example, the petals may be arranged in an irregular or non-repeating order or according to any number of patterns without departing from the spirit and scope of this disclosure. Different applications may involve, for example, different trabecular bone structures including the density and liquid content of the trabecular bone in different bones/areas of the body, the load bearing of the bone, the patient, the nature of the injury, and other considerations discussed herein.

Figure 11:
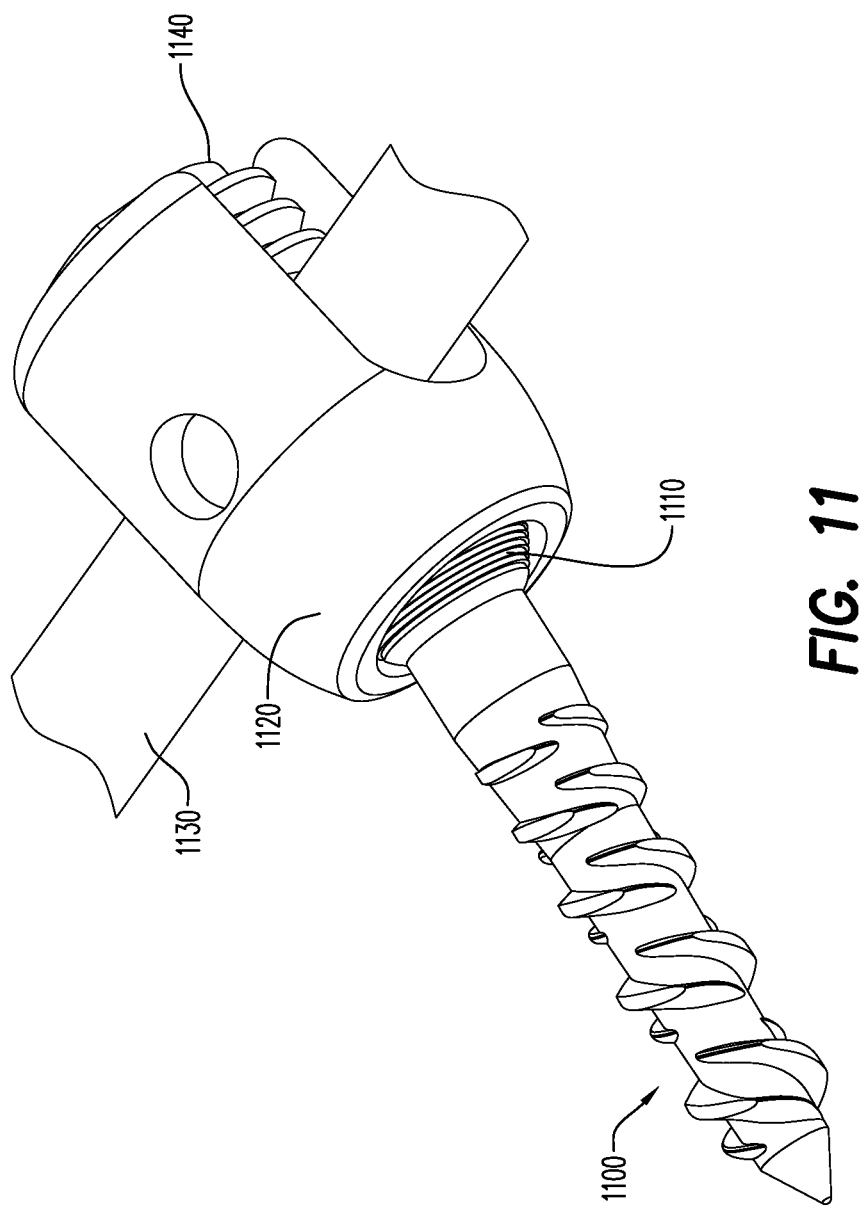
FIG. 11 shows an exemplary surgical system for use with the exemplary orthopedic fastener according to the disclosure.

The exemplary and other embodiments of an orthopedic fastener according to the disclosure may generally be used with known surgical systems for attaching orthopedic fasteners. An exemplary surgical system is shown in FIG. 11. In the exemplary surgical system, an orthopedic fastener 1100 according to the disclosure is attached to a head body 1120 (also called a tulip) by polyaxial joint 1110. The polyaxial joint 1110 is created by, for example, inserting the connecting bulb 308, 908 of the exemplary three-petal 300 and two-petal 900 orthopedic fasteners into the head body 1120. The polyaxial joint 1110 allows the orthopedic fastener 1100 to pivot with respect to the head body 1120. In operation, a user (e.g., surgeon) will insert the orthopedic fastener 1100 into a bone by drilling a hole in one cervical wall of the bone, inserting the orthopedic fastener 1100 into the bone, and turning the orthopedic fastener 1100 using rod 1130 as a handle/torque generator to advance the orthopedic fastener 1100 through the trabecular bone. Set screw 1140 holds the rod 1130 in place within the head body 1120. Set screw 1140 may be any known screw or lock nut, or known device for locking components together. The polyaxial joint 1110 compensates for any differences between the angle at which the orthopedic fastener 1100 is inserted into the bone and the angle at which the rod 1130/head body 1120 are held during the insertion process by allowing the orthopedic fastener 1100 to pivot with respect to the head body 1120 and thereby maintain its trajectory into the bone as the head body 1120 is potentially moved by the surgeon.

Figure 12:
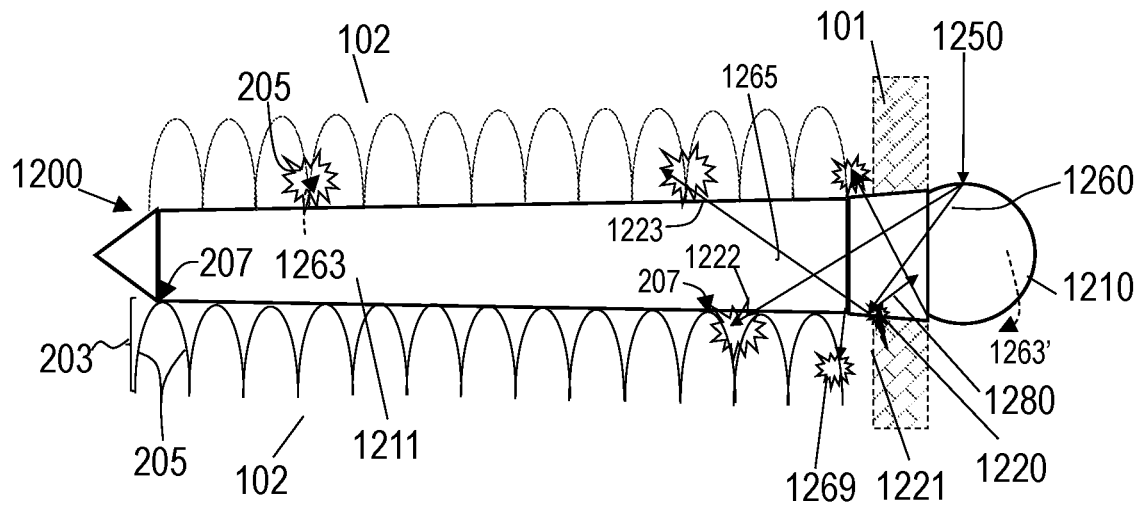
FIG. 12 shows exemplary radial forces in a conventional implant after insertion.
Figure 13:
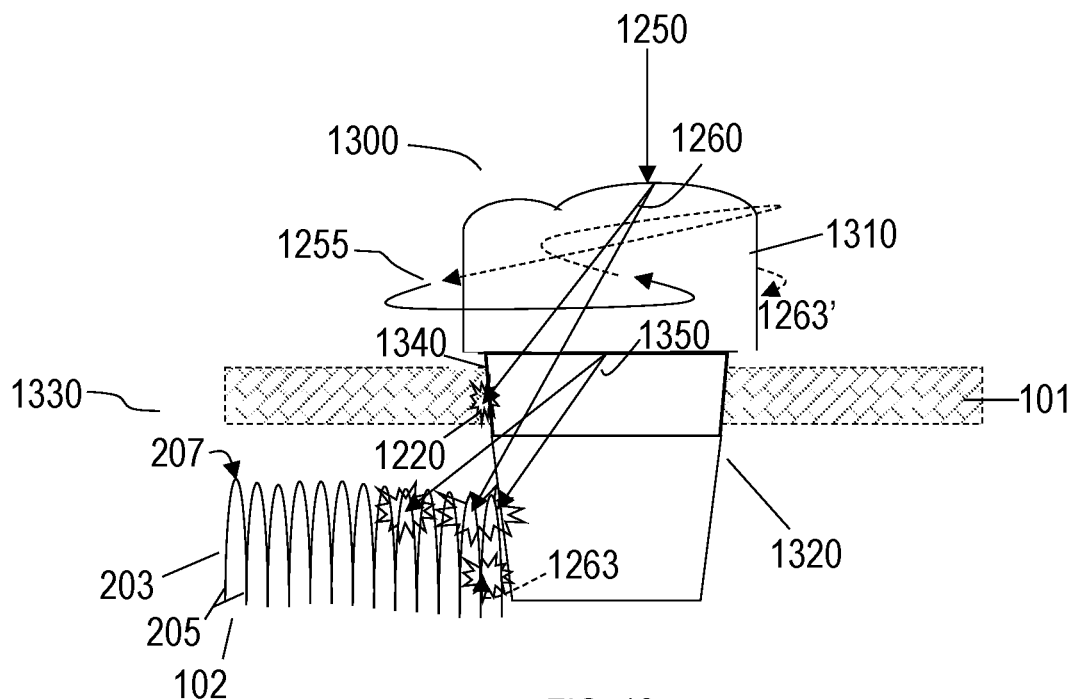
FIG. 13 shows exemplary external and radial forces in a conventional dental implant in a molar region of the jawbone.

With reference now to FIGS. 12 and 13, exemplary illustrations of radial forces, counterforces, and interactions with surrounding bone structure are shown for a conventional fastener inserted into bone. With reference to FIG. 12, an implant 1200 may extend through the cortical wall 101 and into the trabecular bone 102. An external force 1250 from, e.g., body mass, may act on the implant 1200. While the external force 1250 is shown as a single vector, the external force may be a multi-directional force, a circular force, a harmonic force (i.e., with some recurring frequency of occurrence), etc., as discussed above. For purposes of this disclosure, the term "external force" means a force acting on an implant (e.g., an orthopedic fastener 300 according to the exemplary embodiments) after insertion. By way of example only, the external force 1250 may act on the implant 1200 at a portion 1210 that is external to the bone after insertion. As shown in FIG. 12, the external force 1250 diffuses through the fastener and creates radial forces 1260 and/or crushing forces 1269. The radial forces 1260 and crushing forces 1269 may concentrate at a single counterforce point 1220 on the cortical wall 101, e.g., at an interface point or area of the cortical wall 101 and the portion of the implant 1220 passing therethrough, but may also be directed to other counterforce points, e.g., 1222, along the implant. The radial forces 1260 acting on other counterforce points 1222 at which, e.g., the implant is supported or surrounded by trabecular bone 102, may have a direction that points towards and acts on leg portions 205 of the trabecular bone bridges 203. Trabecular bone bridges 203 may be especially susceptible to damage from forces acting at an angle to the leg portions 203 rather than on a direct path to the keystone portion 207. The term "keystone" refers, as with geometric arches, to the highest and most supportive point in the trabecular bone bridge 203 which is shaped generally like a supportive arch. For purposes of this disclosure, "keystone portion" means a portion of the trabecular bone bridge 203 at or near the keystone and correspondingly having a relatively high strength and supportiveness. "Leg portions", on the other hand, refers to the structures extending downwardly away from the keystone portion 207. The terms "keystone portion" and "leg portions" are used to aid in understanding the exemplary embodiments but without limitation to any particular boundaries, dimensions, delineations, or the like.

The radial forces 1260 concentrating at the single counterforce point 1220 may cause microfractures 12221 of the cortical wall 101. The single counterforce point 1220 may counter the radial forces 1260 by, e.g., leveraging the radial forces 1260 by acting as a pivot point for radial movement 1263, 1263' of the implant. The radial movement 1263, 1263' may be a see-saw effect in which the external force 1250 pushes the exposed portion 1210 in the direction 1263' (indicated by dashed arrow) of the external force 1250, and an opposing portion 1211 commensurately moves in an opposite direction 1263 (indicated by dashed arrow). The radial movement 1263, 1263' may also be considered "axial compression" of the trabecular bone 102 and space above the opposing portion 1211, by the opposing portion 1211 moving in the direction 1263.

Compressing the trabecular bone 102 in this manner may weaken and then crush to some degree the trabecular bone bridges 203 and thereby reduce resistance to radial movement 1263, 1263' of the implant 1200. Accordingly, radial resistance may continue to diminish under harmonic radial movement 1263, 1263'. Diminished resistance may, among other things, allow more and a greater degree of radial movement, gradually destroying healthy bone and generating more scar tissue, which increases healing time and decreases the quality of the heal, thereby reducing its ability to continue supporting the implant.

The single counterforce point 1220 may also counter the radial forces 1260 by redirecting 1265 the radial forces 1260 from the single counterforce point 1220 to redirected counterforce points, e.g., 1223. The redirected radial forces 1265 may also have a direction that points towards and/or damages the leg portions 205 of trabecular bone bridges 203 surrounding the redirected counterforce points 1223 and/or resisting radial movement 1263, 1263' of the implant 1200 at or near the redirected counterforce point 1223.

Moreover, a crushing force 1269 may be generated by the external force 1250 pushing the implant 1200 into the cortical wall 101 and/or trabecular bone 102. The crushing force, e.g., 1269, may similarly damage the trabecular bone bridges 203 and/or cortical wall 101, which is relatively brittle.

Some of the radial forces 1260 acting on the single counterforce point 1220 may be redirected 1280 as cancelling radial force 1280. The cancelling radial force 1280 may have a direction that opposes, and thereby balances/cancels the cancelling radial force 1280 and some of the radial forces 1260 from the external force 1250.

With reference to FIG. 13, another exemplary force that may act on an implant may be a harmonic force 1255 having a figure-eight pattern. Exemplary implants that experience this type of force include, without limitation, spinal implants (e.g., implant 1200) and dental implants 1300 set in the molar region of the jaw (as shown and discussed further below with respect to FIG. 13). A spinal implant may experience the harmonic force 1255, e.g., during walking, due to the repetitive leaning, shifting, and rotating movements. A dental implant 1300 may experience the harmonic force during chewing.

With continuing reference to FIG. 13, the dental implant 1300 may include a tooth portion 1310 exposed in a mouth and screw portion 1320 within and anchoring the implant 1300 to the jaw 1330 which may include a cortical wall 101 and trabecular bone 102. As discussed above with respect to FIG. 12, the dental implant 1300 may experience an external force 1250 in a generally downward direction on the tooth portion 1310, due to, e.g., biting, chewing, etc. The external force 1250 may diffuse as radial forces 1260 that diffuse along the dental implant 1300. The radial forces 1260 may cause damage to the cortical wall 101, e.g., at a single counterforce point 1220, and/or the trabecular bone 102, as discussed above. The dental implant 1300 may also experience radial movement 1263, 1263' and, while not shown in FIG. 13, redirected radial forces, and cancelling forces, as discussed above with respect to FIG. 12.

In addition, the harmonic force 1255 may cause omnidirectional radial forces 1350 that may cause damage 1270 in a similar fashion as discussed above. The harmonic force 1255, when applied, constantly causes a wiggle in a circular form and follows a certain frequency. While the harmonic force 1255 illustrated in FIG. 13 has a figure-eight pattern, it is merely exemplary. Harmonic forces may take a number of different patterns depending on, e.g., the cause of the harmonic force and the position and orientation of the implant in the body.

Further, the harmonic force 1255, when applied, may act opposite to the natural movement of the body in the impacted region. Without diffusing these forces through the implant, the majority of the force may likely be absorbed or negated by the relatively thin cortical wall 101, at the insertion point 1340 of the implant (e.g., dental implant 1300). This point may act as a pivot point, as discussed above, that tends to crush if the force exceeds its limit, causing a failure in the construct where the whole screw elongates the canula it resides in. This state may be nearly undetectable and is measured in the micro range. In other cases, it may be visually evident.

Figure 14:
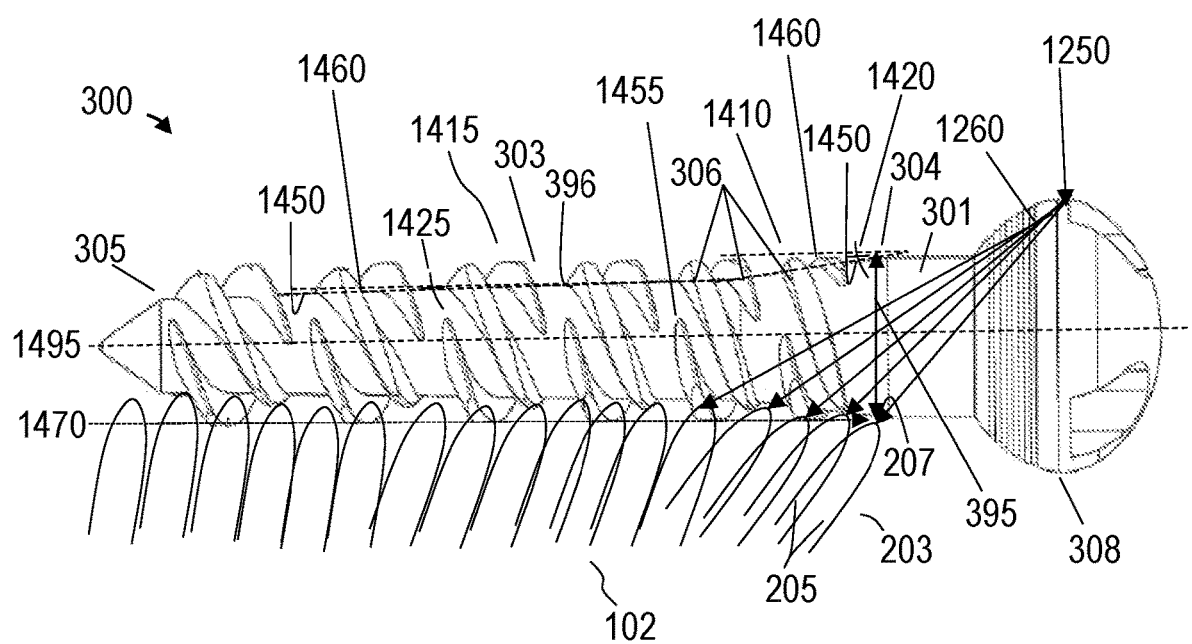
FIG. 14 shows an orthopedic fastener and interactions with bone, according to an exemplary embodiment.

With reference now to FIG. 14, an exemplary embodiment of the orthopedic fastener 300 according to the disclosure is shown. As discussed above, the orthopedic fastener in the exemplary embodiment includes a shaft 303 and a plurality of compound parabolic petals 306 extending helically around the shaft 303. The shaft 303 is connected at the proximal end 304 to a head portion 301 that is positioned between and connected to each of the shaft 303 and the bulb 308. The petals 306 are configured to compress the trabecular bone 102 through which they pass. The degree of compression increases in a direction from the distal end 305 to the proximal end 306 of the shaft 303.

In an aspect, the compressed trabecular bone structure may provide more effective and less damaging countering of radial forces 1260 diffusing through the implant from, e.g., an external force 1250 on the bulb 308. For example, the increased compression of trabecular bone 102 at the proximal end 304 of the shaft 303, due to the exemplary embodiments discussed throughout this disclosure, causes the trabecular bone bridges 203 to shift and tilt, i.e., restructure, as indicated by line 1470, such that more surface area of the trabecular bone structure, including the keystone portions 207, are generally pointing towards the area of increased compression—i.e., towards the proximal end 304 of the shaft 303. The restructuring 1470 of the trabecular bone bridges 203 is a natural physiological response to the compression of the trabecular bone 102. The compression causes the bone at the area of high compression to signal that it is continuously experiencing the higher compression. The signal is physiologically active to indicate that the area of high compression is experiencing a force or condition that may require reinforcement. Accordingly, the physiological response is to point the most supportive portion of the trabecular bone bridge 203, i.e., the keystone portion 207, towards the area of higher compression.

The restructuring 1470 may occur gradually—e.g., over a period of several months. However, as discussed above, compressing the trabecular bone 102 with the exemplary embodiments of an orthopedic fastener 300 according to the disclosure causes less trauma and damage to the trabecular bone 102, leaving a higher density of healthy trabecular bone 102 supporting and surrounding the shaft 303 after insertion. The greater amount and density of healthy trabecular bone 102 may make the signaling and restructuring 1470 response more efficient because more healthy bone is available to signal the compression.

With reference back to FIG. 14, the keystone portions 207 are restructured 1470 such that they are facing towards the area(s) of highest compression, i.e., the proximal end 304 of the shaft 303. As such, the keystone portions 207 are also facing the bulb 308 from which the radial forces 1260 diffuse from the external force 1250 on the bulb 308. The direction to which the keystone portions 207 face may oppose the direction of some radial forces 1260 and/or strengthen the force available for countering the radial forces 1260 at those positions. For example, the relatively strong keystone portions 207 may deflect, absorb, and/or dissipate the radial forces 1260 with greater efficiency, and less damage to the bone structure, than, e.g., trabecular bone bridges 203 oriented such that the radial forces 1260 act on leg portions 205. Cancelling more radial forces 1260 at the regions near the proximal end 304 of the shaft 303, where the trabecular bone 102 is under the greatest compression, may reduce the load on any particular counterforce point, such as a single counterforce point 1220 on the cortical wall 101, to leverage or redirect the radial forces 1260 as radial movement 1263, 1263' or redirected radial forces 1265 that may damage other areas of the bone structure.

In addition, the greater amount and density of healthy trabecular bone available after insertion of the orthopedic fastener 300 (as discussed above) provides more surface area over which the radial forces 1260 may be dissipated. Greater distribution of the radial forces 1260 due to more surface area of the trabecular bone 102 may enhance the resiliency of the trabecular bone 102 and thereby maintain the radial stability and resistance to radial movement of the orthopedic fastener 300 after insertion. Increased radial stability as a natural result from insertion of an orthopedic fastener 300 according to the exemplary embodiments may provide greater flexibility in balancing the need for axial resistance against pull-out forces with the need for resisting radial movement. For example, less structural demands of the orthopedic fastener 300 may be needed for a desired degree of radial resistance/stability.

In other aspects, completing a fixation procedure with the orthopedic fasteners 300 according to the exemplary embodiments may require fewer fixations, and therefore fasteners, than completing the fixation process with conventional screws. For example, a greater amount of remaining, healthy trabecular bone after insertion may provide greater axial and radial resistance per construct. Natural physiological restructuring 1470 of the trabecular bone 102 may provide more efficient cancelling of radial forces 1260 after insertion, which may reduce the number of fasteners required to maintain the resistances over time. Using less fasteners may shorten the recovery time and improve the health and functional utility of the bone structure in adjusting to implants and other changes from the fixation procedure.

Figure 16:
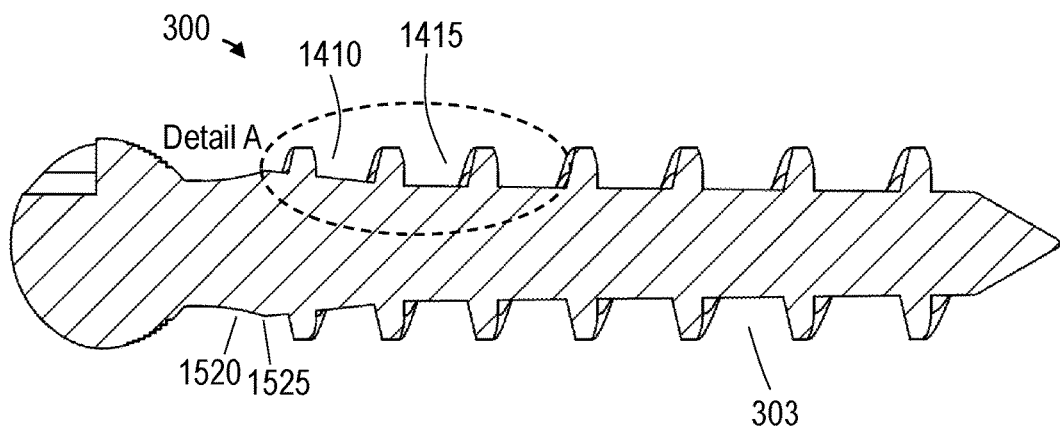
FIG. 16 shows a cross-section of an orthopedic fastener according to an exemplary embodiment.
Figure 17:
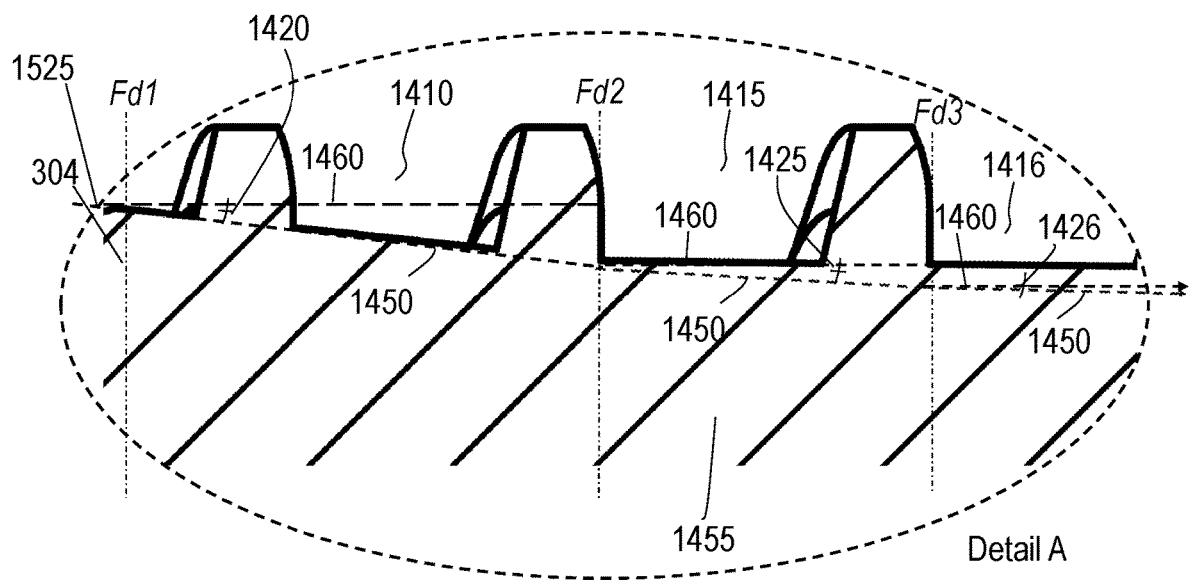
FIG. 17 shows the Detail A region from FIG. 16.

With reference back to FIG. 14, and further reference to FIG. 16 and FIG. 17, the shaft 303, in an aspect, includes a first force diffusion area 1410 positioned at the proximal end 304 of the shaft 303. The first force diffusion area 1410 is dimensioned for directing the radial forces 1260 towards the keystone portions 207 of the trabecular bone bridges 203 compressed against the first force diffusion area 1410. In other words, the shaft 303, as shown in the exemplary embodiment of FIG. 14, includes a double-angle minor diameter—i.e., a first angle minor diameter corresponding to a first diffusion angle 1420 and a second angle minor diameter corresponding to a second diffusion angle 1425. In an aspect, the first diffusion angle 1420 corresponds to an angle at which a surface 1450 of a shaft body 1455, at the roots 396 of the petals 306, extends away and radially inwardly from a horizontal plane 1460 above the shaft body 1455 and extending axially from a common point with the surface 1450 of the shaft body 1455. In other words, the first diffusion angle 1420 corresponds to a rate at which the minor diameter 395 of the shaft 303 decreases in a direction from the proximal end 304 to the distal end 305 of the shaft 303.

For purposes of this disclosure, "radially inwardly" means at least in part towards a center axis 1495 of the orthopedic fastener 300.

The second diffusion angle 1425 is defined as discussed above with respect to the first diffusion angle 1420. However, the second diffusion angle 1425 is different from the first diffusion angle 1420. Accordingly, the portion of the shaft 303 having the second diffusion angle 1425 may be considered a second force diffusion area 1415. In general, but without limitation as to boundaries, dimensions, or delineations, separate force diffusion areas 1410, 1415 may be defined as discrete portions/length of the shaft body 1455 through which the diffusion angle 1420, 1425 is constant. As discussed above, one or more force diffusion areas 1410, 1415 may be dimensioned with a corresponding diffusion angle 1420, 1425 for distributing radial forces 1260 created by forces, such as external force 1250, acting perpendicular to the orthopedic fastener 300. This may allow the forces to be absorbed by a larger cross section of bone and lead the forces away from the thin cortical wall 101 that might otherwise absorb the bulk of the force, potentially at a small point where the force might concentrate. Large forces acting on a small surface of the cortical wall 101 are likely to cause a greater degree of microfracture.

In an aspect, the diffusion angle 1420, 1425 of respective force diffusion areas 1410, 1415 may decrease in a direction from the proximal end 304 to the distal end 305 of the shaft 303. Thus, a force diffusion area 1415 nearer the distal end 305 has a smaller diffusion angle 1425 than a force diffusion area 1410 nearer the proximal end 304. This configuration may gradually reduce the radial force loads propagating from, e.g., the bulb 308 (or, as above, the portion of the orthopedic fastener 300 that is configured for being exposed when the orthopedic fastener 300 is inserted in a bone). A relatively smaller diffusion angle nearer the distal end 305 of the shaft 303 may provide axial resistance against pull-out forces. Increasing diffusion angles in force diffusion areas positioned respectively nearer and nearer to the proximal end 304 of the shaft 303 may progressively balance diffusion of the radial forces 1260, and thereby resistance to radial movement 1263, 1263', in addition to the axial resistance. A force diffusion area positioned at or nearest to the proximal end 304 of the shaft 303 may be dimensioned with a diffusion angle that is primarily, but not necessarily or exclusively, for diffusing the radial forces 1260 and providing radial stability.

Figure 15A:
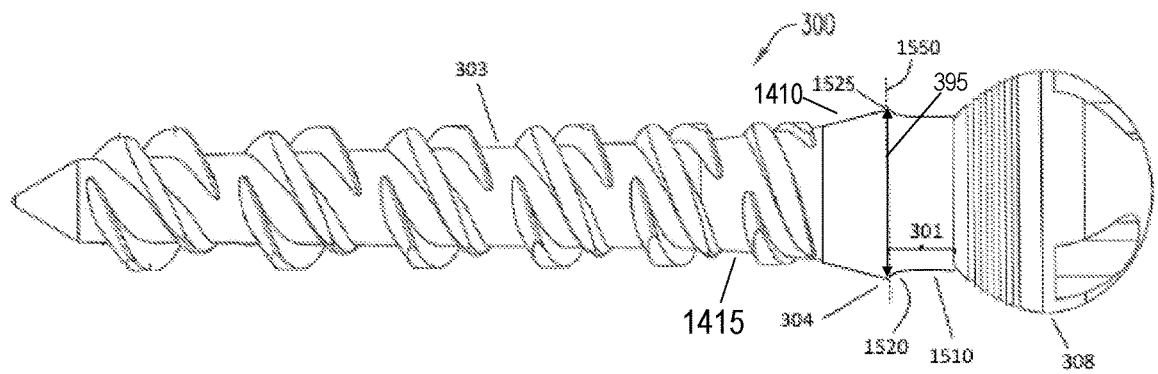
FIG. 15A shows an orthopedic fastener according to an exemplary embodiment.
Figure 15B:
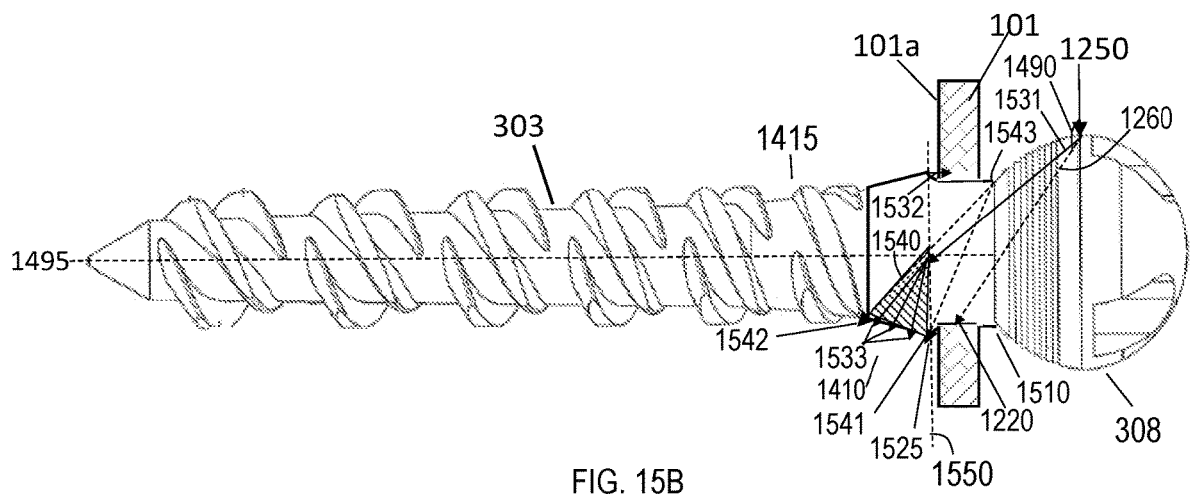
FIG. 15B shows the orthopedic fastener of FIG. 15A inserted in a bone, according to an exemplary embodiment.

With reference now specifically to FIG. 15A and FIG. 15B, an orthopedic fastener 300 according to an exemplary embodiment is shown in isolation (FIG. 15A), and after insertion (FIG. 15B). Features, functions, and aspects common to embodiments discussed above may not be repeated here but are understood to apply to the exemplary embodiment as shown in FIG. 15A and FIG. 15B, to the extent that they are not inconsistent. For example, it will be understood that a first force diffusion area 1410 as shown in FIG. 15A and FIG. 15B is dimensioned with a first diffusion angle 1420 (FIG. 14), for directing radial forces 1260 into the keystone portions 207 of trabecular bone bridges 203 that have restructured 1470 due to increased compression of the trabecular bone bridges 203 against the first force diffusion area 1410 at the proximal end 304 of the shaft 303.

The exemplary embodiment as shown in FIG. 15A and FIG. 15B includes a head portion 301 that includes a neck portion 1510 and a diffusion shoulder region 1520. The first force diffusion area 1410 is positioned at the proximal end 304 of the shaft 303. The diffusion shoulder region 1520 is positioned between and connected to each of the first force diffusion area 1410 and the neck portion 1510. The diffusion shoulder region 1520 extends radially outwardly from the neck portion 1510 and the first force diffusion area 1410 extends radially inwardly from the diffusion shoulder region 1520. For purposes of this disclosure, "radially outwardly" means at least in part away from the center axis 1495 of the orthopedic fastener 300. Terms such as "neck portion" and "diffusion shoulder region" are used to aid in understanding the exemplary embodiments but without limitation as to dimensions, boundaries or delineations.

The diffusion shoulder region 1520 extends to a crest 1525 having a greatest minor diameter 395 of the diffusion shoulder region 1520 and the shaft 303. The first force diffusion area 1401 is positioned at the proximal end 304 of the shaft 303 and is connected to the diffusion should region 1520 at the crest 1525. In an aspect, the diffusion shoulder region 1520 may allow for a more drastic first diffusion angle 1420 of the first force diffusion area 1410 and, in certain aspects, may provide a structure that may contact the cortical wall 101 to assist in providing resistance against axial pull-out forces and radial movement 1263, 1263' (i.e., the see-saw effect) about a counterforce point or area (i.e., 1220) as a pivot point, caused by harmonic application of an external force (e.g., external force 1250). For example, the diffusion shoulder region 1520 may allow the first force diffusion area 1401 to extend radially inwardly from a higher point (i.e., a greater minor diameter), e.g., at the crest 1525.

FIG. 15B illustrates, among other things, an exemplary revectoring of radial forces diffusing through the exemplary orthopedic fastener 300, according to the exemplary embodiment shown in FIG. 15B. The exemplary illustration in FIG. 15B is to aid in understanding the exemplary embodiments, without limitation as to any particular force distribution, direction, dimension, etc.

In an aspect, the first force diffusion area 1410 extends along a length of the shaft 303 between a first end vector 1541 and a second end vector 1542. Each of the first end vector 1541 and the second end vector 1542 extends from an outside-top neck position 1543 of the neck portion 1510. In other words, the last diameter position of the neck portion 1510 that may be inserted into the cortical wall 101. The first end vector 1541 extends from the outside-top neck position 1543 to the crest 1525 of the diffusion shoulder region 1520. The second end vector 1542 extends between the outside-top neck position 1543 and the point on the shaft 303 at which the diffusion angle changes from the first diffusion angle 1420 (FIG. 17) of the first force diffusion area 1410. A first force diffusion space 1540 may be defined, by way of example and without limitation, as a radial area of the head portion 301 bounded by a plane 1550 containing the crest 1525 of the diffusion shoulder region 1520 and a plane containing the second end vector 1541. In an aspect, the exemplary embodiment of an orthopedic fastener 300 as shown in FIG. 15B is dimensioned to position the force diffusion space 1540, i.e., the crest 1525 of diffusion shoulder region 1520, as close as possible to an inner surface 101a of the cortical wall 101 after insertion into the bone, to commensurately place the first force diffusion area 1410 closer to, e.g., the bulb 308 and external force 1250 acting on it. In an exemplary configuration, the force diffusion space 1540 is not farther than about 2 mm from the inner surface 101a of the cortical wall 101.

With continuing reference to FIG. 15B, in one aspect, the external force 1250 from, e.g., body weight, may, in conventional implants (see FIG. 12), create radial and/or crushing forces 1260 that may be concentrated onto a single counterforce point/area 1220 on the cortical wall 1210, at an interface with a portion of the implant. According to the exemplary embodiment shown in FIGS. 15A and 15B, a reverse force 1532 opposing the external force 1250 may be generated and extend from, in one aspect, the crest 1525 of the diffusion shoulder region 1520, and back towards the external force 1520 acting on the bulb 308, in response to the external force 1250 acting, e.g., in the illustration of FIG. 15B, downwardly on the bulb 380. The reverse force 1532 may, in one aspect, cancel a portion of the external force 1250. The reverse force 1532 may also revector at least a portion of the radial/crushing force 1260 on an oblique angle 1490, as a revectored force 1531 in a direction away from the cortical wall 101 and, e.g., the single counterforce point/area 1220, and towards the first force diffusion area 1410.

Upon encountering the first force diffusion area radius (i.e., the plane 1550 containing the crest 1525 of the diffusion shoulder region), the revectored force 1531 may be distributed by the first force diffusion space 1540, into distributed forces 1533 across the first force diffusion area 1410 and corresponding surface area of trabecular bone 102, including the keystone portions 207 of the trabecular bone bridges 203, that are compressed against the first force diffusion area 1410. In such manner, the radial force 1260 may be distributed across a greater degree of surface area of trabecular bone 102, and the keystone portions 207, than may be available in conventional fasteners. The greater distribution of the radial force 1260, and the relatively high strength of the keystone portions 207 tilted to encounter the radial force 1260, may reduce the degree to which, e.g., the radial force 1260 damages the trabecular bone 102 and/or the cortical wall 101, gets redirected 1265 to other areas of the shaft 303, and/or leads to a see-saw effect (radial movement) 1263, 1263' of the orthopedic fastener 303.

With continuing reference to FIG. 15A and FIG. 15B, and additional reference to FIG. 16 and FIG. 17, the second force diffusion area 1415 according to the exemplary embodiments discussed throughout the disclosure is dimensioned with the second diffusion angle 1425 that is less than the first diffusion angle 1420. According to an exemplary embodiment, the first diffusion angle 1420 is between approximately 2 degrees and approximately 45 degrees. In the same or a different embodiment, the second diffusion angle 1420 is less than the first diffusion angle and may be calculated based on the compression achieved by the design of the first diffusion angle 1420. This first diffusion angle 1420, in an exemplary embodiment and without limitation, is approximately 16 degrees. For purposes of this disclosure, certain measurements are provided, without limitation, as a single value or a range of values, to set forth and aid in understanding certain exemplary embodiments and features. It is understood that such values, regardless of the presence or absence of modifying language, are not limited to the absolute value(s) but include a range that includes the measurement(s) and is understood to accomplish the configuration, features, and function to which the measurement(s) relate, consistent with the disclosure. With respect to, e.g., diffusion angles (e.g., 1420, 1425) of the shaft 303, the drawings may not be drawn to scale, but are presented for illustrating, generally, certain features of the exemplary embodiments.

Notwithstanding the above, the term "approximately" may be used for clarity regarding the non-limiting exemplary measurements and ranges. Thus, the term "approximately" when used with measurement(s) similarly means the express measurement(s) or a range including the measurement(s) and understood to accomplish the configuration, features, and function to which the measurement(s) relate, consistent with the disclosure. It is understood that the term "approximately" does not otherwise limit expressions of measurement that may not appear beside "approximately".

The second force diffusion area 1415 is positioned between the first force diffusion area 1410 and the distal end 305 of the shaft 303. The second force diffusion area 1415 is dimensioned with the second diffusion angle 1425 for one of contributing to axial resistance of the orthopedic fastener 300 inserted in a bone and redirecting/distributing radial forces 1260 to the keystone portions 207 of trabecular bone 102 tilted towards the proximal end 304 of the shaft 303 and compressed against the second force diffusion area 1415.

According to the exemplary embodiments, the second diffusion angle 1425 is less than the first diffusion angle 1420. For example, and without limitation, the second diffusion angle 1425 may be between approximately 0.5 degrees and approximately 22 degrees. In an exemplary embodiment, without limitation, the first diffusion angle 1420 may be between approximately 2 degrees and approximately 45 degrees and the second diffusion angle 1425 may be between approximately 0.5 degrees and approximately 22 degrees.

With reference now to FIG. 16, a cross-sectional view of an exemplary embodiment of the orthopedic fastener 300 is shown. FIG. 17 is a blowup showing the portion of FIG. 16 labeled 'Detail A'. With reference to FIGS. 16 and 17, the shaft 303 includes the first force diffusion area 1410 dimensioned with the first diffusion angle 1420 and the second force diffusion area 1415 dimensioned with the second diffusion angle 1425.

FIG. 17 shows the first diffusion angle 1420 and the second diffusion angle 1425 respectively at the first force diffusion area 1410 and a portion of the second force diffusion area 1415. The exemplary embodiment shown in FIG. 17 includes a hypothetical third force diffusion area 1416 positioned between the second force diffusion area 1415 and the distal end 305 of the shaft 303. The second force diffusion area 1415 and the third force diffusion area 1416 are illustrated with dashed lines to indicate the hypothetical configuration and illustrate an exemplary embodiment of the orthopedic fastener 300. The hypothetical configuration is indicated by dashed lines representing the second diffusion angle 1425 and a third diffusion angle 1426, including a hypothetical corresponding surface 1450 of the shaft body portion 1455 and a reference horizontal line 1460 for each of the second force diffusion area 1415 and the third force diffusion area 1416. While the surface 1450 of the shaft body portion 1455 and the reference horizontal line 1460 are also shown in dashed lines for the first force diffusion area 1410 and first diffusion angle 1420, those dashed lines do not represent a hypothetical configuration. Those lines, with respect to the first force diffusion area 1410, are for more clearly illustrating the first diffusion angle 1420 and the first force distribution area 1410, and the relationship of those aspects with other aspects of the exemplary embodiment.

The third force diffusion area 1416 is dimensioned with the third diffusion angle 1426 and may contribute to axial resistance and/or diffusion of radial forces. Regarding diffusion of radial forces, the third force diffusion area 1416 may redirect/distribute radial forces 1260 to keystone 207 portions of trabecular bone 102 compressed against the third force diffusion area 1416. The third diffusion angle 1426 in the exemplary embodiment is less than the second diffusion angle 1425. The third force diffusion area 1416 may extend all the way from the second force diffusion area 1415 to the distal end 305 of the shaft 303, or the shaft 303 may include one or more additional force diffusion areas, distal to the third force diffusion area 1416, and with diffusion angles that are smaller than the third diffusion angle 426.

In an aspect, each force diffusion area 1410, 1415, 1416 may be defined in part by respective lengths of the shaft 303 along which the diffusion angle 1420, 1425, 1426 is constant. For example, and with reference to the exemplary embodiment shown in FIG. 17, the first force diffusion area 1410 extends from a first transition position Fd1 representing the position at which the proximal end 304 of the shaft 303 connects to and extends radially inwardly from the crest 1525 of the shoulder diffusion region 1520. The second force diffusion area 1415 extends from a second transition position Fd2 at which the shaft body portion 1455 transitions from a length of the shaft body portion 1455 having the first diffusion angle 1420 to a length of the shaft body portion 1455 having the second diffusion angle 1425. The second force diffusion area 1415 extends to a third transition portion Fd3 at which the shaft body portion 1455 transitions from a length of the shaft body portion 1455 having the second diffusion angle 1425 to a length of the shaft body portion 1455 having the third diffusion angle 1426. The third force diffusion area 1416 may extend from the third transition position Fd3 to a further, distal force diffusion area or the distal end 305 of the shaft 303.

In an aspect of the exemplary embodiment shown in FIG. 17, and without limitation, the third diffusion angle may be between approximately 0.5 degrees and approximately 6 degrees. In the same or another embodiment, the first diffusion angle 1420 may be between approximately 2 degrees and approximately 45 degrees. The second diffusion angle 1425 may be between approximately 0.5 degrees and approximately 22 degrees. The third diffusion angle 1426 may be between approximately 0.5 degrees and approximately 6 degrees.

In the same or other embodiments, the first diffusion angle 1420 may be approximately 22 degrees, the second diffusion angle 1425 may be approximately 16 degrees, and the third diffusion angle 1426 may be approximately 3 degrees.

Selecting each diffusion angle along the shaft in a particular embodiment requires multiple considerations. For example, the greatest angles may be used, without limitation, in relatively short fasteners that may experience omnidirectional forces—e.g., the dental implant 1300 in a molar region. Such fasteners must distribute forces that are diffusing through the fastener along vectors and profiles that may extend in nearly any radial direction and to nearly any axial position along the length of the fastener, and the length of the fastener may be relatively short such that each force diffusion area must direct/distribute a substantial amount of the force(s).

In a similar respect, the availability of bone in an implant region may be considered. For example, more jawbone is typically available for implants at cutting teeth positions than molar positions, and a dental implant for regions with more jawbone may have a relatively greater length along which force(s) may diffuse. Moreover, the typical differences in expected forces may be considered such as bi-directional in cutting teeth vs. omnidirectional in the molar region.

As discussed above, the nature of the forces is a consideration. For example, harmonic, circular forces (e.g., in the dental implant 1300 in the molar region) may require greater diffusion angles because of the high degree of omnidirectional forces through which the harmonic, circular forces are diffused through the orthopedic fastener, and the tendency of harmonic, circular forces to place a particularly significant stress on cortical walls. Vectored and/or bidirectional forces may require smaller angles, by comparison, as the vectored and/or bidirectional forces may diffuse in a more broadly distributed fashion along the fastener. Moreover, in fasteners with a length that may accommodate multiple relatively long force diffusion areas, the diffusion angle of individual force diffusion areas may be relatively small, because more length of the fastener provides greater distribution of force(s) diffusing through the fastener.

By way of example only, one or more diffusion angles of force diffusion areas for a vertebral implant may be between approximately 2 degrees and approximately 22 degrees. For a hip implant, which requires longer fasteners, the shaft 303 may have more than 3 force diffusion areas and ranges of the corresponding diffusion angles of the shaft may be, progressively from the proximal end to the distal end of the shaft: 1) between approximately 30 degrees and approximately 45 degrees; 2) between approximately 22 degrees and approximately 30 degrees; 3) between approximately 14 degrees and approximately 22 degrees; and 4) between approximately 3 degrees and approximately 4 degrees.

In a further aspect, the disclosure relates to a method for orthopedic fastening. The method may include inserting an orthopedic fastener 300 according to the exemplary embodiments discussed throughout this disclosure, into a bone.

Consistent with the exemplary embodiments, the orthopedic fastener 300 may include the shaft 303 and the plurality of compound parabolic petals 306 extending helically around the shaft 303. The method may further include compressing trabecular bone 102 between the petals 306, in response to inserting the orthopedic fastener 300 into the bone.

In a further aspect of the exemplary method, the shaft 303 may include a force diffusion area 1410 dimensioned with a diffusion angle 1420 for distributing a radial force to keystone 207 portions of trabecular bone 102 compressed against the force diffusion area 1410, as discussed with respect to certain exemplary embodiments.

The exemplary devices, systems, and methods disclosed herein are not limited to the specific embodiments described, but rather, features illustrated or described as part of one embodiment can be used on or in conjunction with other embodiments to yield yet a further embodiment. The disclosure is intended to include such modifications and variations. Further, steps described in, e.g., methods of manufacture and/or use may be conducted independently and separately from other steps described herein.

The present disclosure, in various embodiments, configurations and aspects, includes components, methods, processes, systems and/or apparatus substantially developed as depicted and described herein, including various embodiments, sub-combinations, and subsets thereof. The present disclosure, in various embodiments, configurations and aspects, includes providing devices and processes in the absence of items not depicted and/or described herein or in various embodiments, configurations, or aspects hereof, including in the absence of such items as may have been used in previous devices or processes, e.g., for improving performance, achieving ease and/or reducing cost of implementation.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

In this specification and the claims that follow, reference will be made to a number of terms that have the following meanings. The terms "a" (or "an") and "the" refer to one or more of that entity, thereby including plural referents unless the context clearly dictates otherwise. As such, the terms "a" (or "an"), "one or more" and "at least one" can be used interchangeably herein. Furthermore, references to "one embodiment", "some embodiments", "an embodiment" and the like are not intended to be interpreted as excluding the existence of additional embodiments that also incorporate the recited features. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Terms such as "first," "second," "upper," "lower" etc. are used to identify one element from another, and unless otherwise specified are not meant to refer to a particular order or number of elements.

Where necessary, exemplary ranges have been supplied, and those ranges are inclusive of all sub-ranges there between. Variations in the ranges for particular applications of the devices, systems, and methods according to the disclosed considerations may be varied according to a variety of factors including but not limited to the particular application for, e.g, different bones and/or locations such as spinal and/or other bone locations including but not limited to dental applications, facial or cosmetic applications, and or/other applications in which bone fastening and stabilization is necessary. The ranges may also depend on, for example, the age and condition of the patient, the forces that will act upon the fastener, the general level of activity of the patient, etc. The exemplary embodiments in this disclosure do not limit the use of the exemplary orthopedic fastener for any applications in which trauma to bone, or, in particular, trabecular bone is desired.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable, or suitable. For example, in some circumstances an event or capacity can be expected, while in other circumstances the event or capacity cannot occur—this distinction is captured by the terms "may" and "may be."

As used in the claims, the word "comprises" and its grammatical variants logically also subtend and include phrases of varying and differing extent such as for example, but not limited thereto, "consisting essentially of" and "consisting of."

The terms "determine", "calculate" and "compute," and variations thereof, as used herein, are used interchangeably and include any type of methodology, process, mathematical operation or technique.

The present disclosure has been presented for purposes of illustration and description and is not intended to limit the present disclosure to the form or forms disclosed herein. In the foregoing Detailed Description for example, various features of the present disclosure are grouped together in one or more embodiments, configurations, or aspects for the purpose of streamlining the disclosure. The features of the embodiments, configurations, or aspects of the present disclosure may be combined in alternate embodiments, configurations, or aspects other than those discussed above. This method of disclosure is not to be interpreted as reflecting an intention that the present disclosure requires more features than are expressly recited in each claim. Rather, as the following claims reflect, the claimed features may lie in less than all features of a single foregoing disclosed embodiment, configuration, or aspect. Thus, the following claims are hereby incorporated into this Detailed Description, with each claim standing on its own as a separate embodiment of the present disclosure.

Advances in science and technology may make substitutions possible that are not now contemplated by reason of the imprecision of language; these variations should be covered by the appended claims. Further, while this disclosure sets forth certain exemplary embodiments, various changes may be made and features may be substituted without departing from the contemplated scope. In addition, many modifications may be made to adapt a particular situation or material to this disclosure without departing from the essential scope thereof.

What is claimed is:

1. An orthopedic fastener, comprising:
   a shaft; and
   a plurality of compound parabolic petals extending helically around the shaft, wherein the petals are configured to compress trabecular bone.

2. The orthopedic fastener of claim 1, wherein the shaft includes a force diffusion area, and the force diffusion area is dimensioned for distributing a radial force towards keystone portions of trabecular bone compressed against the force diffusion area.

3. The orthopedic fastener of claim 2, wherein the radial force is a force from a harmonic force applied to a portion of the orthopedic fastener that is configured for being exposed from a bone, when the orthopedic fastener is inserted in the bone.

4. The orthopedic fastener of claim 2, further comprising a neck portion and a diffusion shoulder region, wherein
   the force diffusion area is positioned at a proximal end of the shaft,
   the diffusion shoulder region is positioned between and connected to each of the force diffusion area and the neck portion,
   the diffusion shoulder region extends radially outwardly from the neck portion and the force diffusion area extends radially inwardly from the diffusion shoulder region.

5. The orthopedic fastener of claim 4, wherein the force diffusion area is dimensioned with a diffusion angle for distributing the radial force towards the keystone portions of the trabecular bone compressed against the force diffusion area.

6. The orthopedic fastener of claim 5, wherein the diffusion angle is between approximately 2 degrees and approximately 45 degrees.

7. The orthopedic fastener of claim 5, wherein the diffusion angle is approximately 16 degrees.

8. An orthopedic fastener, comprising:
   a head portion;
   a shaft including a proximal end, a distal end, and a first force diffusion area positioned at the proximal end of the shaft, wherein the first force diffusion area is connected to the head portion and extends radially inwardly from the head portion; and
   a plurality of compound parabolic petals extending helically around the shaft, wherein the petals are configured to compress trabecular bone, wherein
   the first force diffusion area is dimensioned for distributing a first radial force towards keystone portions of trabecular bone compressed against the first force diffusion area.

9. The orthopedic fastener of claim 8, wherein the head portion includes a neck portion and a diffusion shoulder region, wherein the diffusion shoulder region is positioned between and connected to each of the first force diffusion area and the neck portion, the diffusion shoulder region extends radially outwardly from the neck portion, and the first force diffusion area extends radially inwardly from the diffusion shoulder region.

10. The orthopedic fastener of claim 9, wherein the first force diffusion area is dimensioned with a first diffusion angle for distributing the first radial force towards the keystone portions of the trabecular bone compressed against the first force diffusion area.

11. The orthopedic fastener of claim 10, wherein the shaft further includes a second force diffusion area positioned between the first force diffusion area and the distal end of the shaft, wherein the second force diffusion area is dimensioned with a second diffusion angle for distributing a second radial force towards the keystone portions of trabecular bone compressed against the second force diffusion area.

12. The orthopedic fastener of claim 11, wherein the second diffusion angle is less than the first diffusion angle.

13. The orthopedic fastener of claim 12, wherein the first diffusion angle is between approximately 2 degrees and approximately 45 degrees.

14. The orthopedic fastener of claim 12, wherein the second diffusion angle is between approximately 0.5 degrees and approximately 22 degrees.

15. The orthopedic fastener of claim 12, wherein the shaft further includes a third force diffusion area positioned between the second force diffusion area and the distal end of the shaft, wherein the third force diffusion area is dimensioned with a third diffusion angle for distributing a third radial force towards keystone portions of trabecular bone compressed against the third diffusion area, and the third diffusion angle is less than the second diffusion angle.

16. The orthopedic fastener of claim 15, wherein the first diffusion angle is approximately 22 degrees, the second diffusion angle is approximately 16 degrees, and the third diffusion angle is approximately 3 degrees.

17. The orthopedic fastener of claim 12, wherein the shaft further includes a third force diffusion area positioned between the second force diffusion area and the distal end of the shaft, wherein the third force diffusion area is dimensioned with a third diffusion angle for distributing a third radial force towards keystone portions of trabecular bone compressed against the third diffusion area, and the third diffusion angle is between approximately 0.5 degrees and approximately 6 degrees.

18. The orthopedic fastener of claim 8, wherein the radial force is a force from a harmonic force applied to a portion of the orthopedic fastener that is configured for being exposed from a bone, when the orthopedic fastener is inserted in the bone.

19. A method for orthopedic fastening, comprising:
   inserting an orthopedic fastener into a bone, wherein the orthopedic fastener includes a shaft and a plurality of compound parabolic petals extending helically around the shaft; and
   compressing trabecular bone between the petals, in response to inserting the orthopedic fastener into the bone.

20. The method of claim 19, wherein the shaft includes a force diffusion area dimensioned for distributing a radial force towards keystone portions of trabecular bone compressed against the force diffusion area.

* * * * *